(12) United States Patent
Reid et al.

(10) Patent No.: US 11,999,973 B2
(45) Date of Patent: Jun. 4, 2024

(54) METHOD FOR PRODUCING RECOMBINANT ONCOLYTIC ADENOVIRUS WITH MODIFIED E1A CANCER-SPECIFIC PROMOTER

(71) Applicant: EpicentRx, Inc., La Jolla, CA (US)

(72) Inventors: Tony R. Reid, San Diego, CA (US); Bryan T. Oronsky, Los Altos Hills, CA (US); Christopher Larson, San Diego, CA (US)

(73) Assignee: EPICENTRX, INC., La Jolla, CA (US)

( * ) Notice: Subject to any disclaimer, the term of this patent is extended or adjusted under 35 U.S.C. 154(b) by 842 days.

(21) Appl. No.: 16/604,194

(22) PCT Filed: Apr. 10, 2018

(86) PCT No.: PCT/US2018/026977
§ 371 (c)(1),
(2) Date: Oct. 10, 2019

(87) PCT Pub. No.: WO2018/191313
PCT Pub. Date: Oct. 18, 2018

(65) Prior Publication Data
US 2020/0032223 A1    Jan. 30, 2020

Related U.S. Application Data

(60) Provisional application No. 62/483,837, filed on Apr. 10, 2017.

(51) Int. Cl.
*C12N 7/00* (2006.01)

(52) U.S. Cl.
CPC ...... *C12N 7/00* (2013.01); *C12N 2710/10321* (2013.01); *C12N 2710/10322* (2013.01); *C12N 2710/10332* (2013.01); *C12N 2710/10352* (2013.01)

(58) Field of Classification Search
CPC ............ C12N 7/00; C12N 2710/10321; C12N 2710/10322; C12N 2710/10332
See application file for complete search history.

(56) References Cited

U.S. PATENT DOCUMENTS

| 6,113,913 | A | 9/2000 | Brough et al. |
| 9,073,980 | B2 * | 7/2015 | Reid .................. C12N 7/00 |
| 2005/0153419 | A1 | 7/2005 | Liu et al. |
| 2019/0352669 | A1 * | 11/2019 | Reid .................. A61P 9/12 |

FOREIGN PATENT DOCUMENTS

| JP | 2007515172 A | 6/2007 |
| WO | WO-2000032754 A1 | 6/2000 |
| WO | WO-2003039459 A2 | 5/2003 |
| WO | WO-2005063910 A1 | 7/2005 |
| WO | WO-2010101921 A2 | 9/2010 |

OTHER PUBLICATIONS

Longley, Jr., R., et al., 2005 Development of a serum-free suspension process for the production of a conditionally replicating adenovirus using A549 cells, Cytotechnol. 49:161-171.*
Gilbert, R., et al., 2014, Establishment and validation of new complementing cells for production of E1-deleted adenovirus vectors in serum-free suspension culture, J. Virol. Methods 208:177-188.*
Niemann, J., and F. Kuhnel, 2017, Oncolytic viruses: adenoviruses, Virus Genes 53:700-706.*
Belluti, S., et al., 2020, Transcription factors in cancer: When alternative splicing determines opposite cell fates, Cells 9(760):9030760, pp. 1-28.*
Stewart, P. L., 2016, Adenovirus structure, in Adenoviral Vectors for Gene Therapy, Elsevier, Inc., http://dx.doi.org/10.1016/B978-0-11-800276-6.00001-2, pp. 1-26.*
Hedjran, F., et al., 2011, Deletion Analysis of Ad5 E1a Transcriptional Control Region: Impact on Tumor-Selective Expression of E1a and E1b, Cancer Gene Therapy 18:717-723.*
Feng et al., (1997). "Stable in vivo gene transduction via a novel adenoviral/retroviral chimeric vector," Nature Biotechnology, 15:866-870.
International Search Report and Written Opinion received for International Patent Application No. PCT/US2018/026977 dated Jul. 16, 2018, 11 pages.
Kirn, (2000). "Replication-selective oncolytic adenoviruses: virotherapy aimed at genetic targets in cancer," Oncogene, 19(56):6660-6669.
Kirn, (2001). "Oncolytic virotherapy for cancer with the adenovirus dl1520 (Onyx-015): results of phase I and II trials," Expert Opinion On Biological Therapy, 1(3):525-538.
Kumar et al., (2008). "Virus combinations and chemotherapy for the treatment of human cancers," Current Opinion In Molecular Therapeutics, 10(4):371-379.
Ramachandra et al., (2001). "Re-engineering adenovirus regulatory pathways to enhance oncolytic specificity and efficacy," Nature Biotechnology, 19:1035-1041.

* cited by examiner

*Primary Examiner* — Jeffrey S Parkin
(74) *Attorney, Agent, or Firm* — Morrison & Foerster LLP

(57) ABSTRACT

The invention relates to a method for producing a recombinant virus, e.g., a recombinant oncolytic adenovirus, using an A549 host cell.

23 Claims, 3 Drawing Sheets

Specification includes a Sequence Listing.

SEQUENCE LISTING

<160> NUMBER OF SEQ ID NOS: 14

<210> SEQ ID NO 1
<211> LENGTH: 35938
<212> TYPE: DNA
<213> ORGANISM: Adenovirus type 5

<400> SEQUENCE: 1

```
catcatcaat aatatacctt attttggatt gaagccaata tgataatgag ggggtggagt      60
ttgtgacgtg gcgcggggcg tgggaacggg gcgggtgacg tagtagtgtg gcggaagtgt     120
gatgttgcaa gtgtggcgga acacatgtaa gcgacggatg tggcaaaagt gacgtttttg     180
gtgtgcgccg gtgtacacag gaagtgacaa ttttcgcgcg gttttaggcg gatgttgtag     240
taaatttggg cgtaaccgag taagatttgg ccatttttcgc gggaaaactg aataagagga     300
agtgaaatct gaataatttt gtgttactca tagcgcgtaa tatttgtcta gggccgcggg     360
```

```
gactttgacc gtttacgtgg agactcgccc aggtgttttt ctcaggtgtt ttccgcgttc    420
cgggtcaaag ttggcgtttt attattatag tcagctgacg tgtagtgtat ttatacccgg    480
tgagttcctc aagaggccac tcttgagtgc cagcgagtag agttttctcc tccgagccgc    540
tccgacaccg ggactgaaaa tgagacatat tatctgccac ggaggtgtta ttaccgaaga    600
aatggccgcc agtcttttgg accagctgat cgaagaggta ctggctgata atcttccacc    660
tcctagccat tttgaaccac ctacccttca cgaactgtat gatttagacg tgacggcccc    720
cgaagatccc aacgaggagg cggtttcgca gattttttcc gactctgtaa tgttggcggt    780
gcaggaaggg attgacttac tcacttttcc gccggcgccc ggttctccgg agccgcctca    840
cctttcccgg cagcccgagc agccggagca gagagccttg ggtccggttt ctatgccaaa    900
ccttgtaccg gaggtgatcg atcttacctg ccacgaggct ggcttccac ccagtgacga     960 cgaggatgaa gagggtgagg agtttgtgtt agattatgtg gagcaccccg ggcacggttg   1020
caggtcttgt cattatcacc ggaggaatac gggggaccca gatattatgt gttcgctttg   1080
ctatatgagg acctgtggca tgtttgtcta cagtaagtga aaattatggg cagtgggtga   1140
tagagtggtg ggtttggtgt ggtaattttt ttttaatttt ttacagtttt gtggtttaaa   1200
gaattttgta ttgtgatttt tttaaaaggt cctgtgtctg aacctgagcc tgagcccgag   1260
ccagaaccgg agcctgcaag acctacccgc cgtcctaaaa tggcgcctgc tatcctgaga   1320
cgcccgacat cacctgtgtc tagagaatgc aatagtagta cggatagctg tgactccggt   1380
ccttctaaca cacctcctga gatacacccg gtggtcccgc tgtgccccat taaaccagtt   1440
gccgtgagag ttggtgggcg tcgccaggct gtggaatgta tcgaggactt gcttaacgag   1500
cctgggcaac ctttggactt gagctgtaaa cgccccaggc cataaggtgt aaacctgtga   1560
ttgcgtgtgt ggttaacgcc tttgtttgct gaatgagttg atgtaagttt aataaagggt   1620
gagataatgt ttaacttgca tggcgtgtta aatggggcgg ggcttaaagg gtatataatg   1680
cgccgtgggc taatcttggt tacatctgac ctcatggagg cttgggagtg tttggaagat   1740
ttttctgctg tgcgtaactt gctggaacag agctctaaca gtacctcttg gttttggagg   1800
tttctgtggg gctcatccca ggcaaagtta gtctgcagaa ttaaggagga ttacaagtgg   1860
gaatttgaag agcttttgaa atcctgtggt gagctgtttg attctttgaa tctgggtcac   1920
caggcgcttt tccaagagaa ggtcatcaag actttggatt tttccacacc ggggcgcgct   1980
gcggctgctg ttgctttttt gagttttata aaggataaat ggagcgaaga aacccatctg   2040 agcgggggt acctgctgga ttttctggcc atgcatctgt ggagagcggt tgtgagacac    2100
aagaatcgcc tgctactgtt gtcttccgtc cgcccggcga taataccgac ggaggagcag   2160
cagcagcagc aggaggaagc caggcggcgg cggcaggagc agagcccatg gaacccgaga   2220
gccggcctgg accctcggga atgaatgttg tacaggtggc tgaactgtat ccagaactga   2280
gacgcatttt gacaattaca gaggatgggc aggggctaaa gggggtaaag agggagcggg   2340
gggcttgtga ggctacagag gaggctagga atctagcttt tagcttaatg accagacacc   2400
gtcctgagtg tattactttt caacagatca aggataattg cgctaatgag cttgatctgc   2460
tggcgcagaa gtattccata gagcagctga ccacttactg gctgcagcca ggggatgatt   2520
ttgaggaggc tattagggta tatgcaaagg tggcacttag gccagattgc aagtacaaga   2580
tcagcaaact tgtaaatatc aggaattgtt gctacatttc tgggaacggg gccgaggtgg   2640
agatagatac ggaggatagg gtggccttta gatgtagcat gataaatatg tggccgggg    2700 tgcttggcat ggacgggtg gttattatga atgtaaggtt tactggcccc aattttagcg     2760
```

```
gtacggtttt cctggccaat accaaccttga tcctacacgg tgtaagcttc tatgggttta    2820
acaatacctg tgtggaagcc tggaccgatg taagggttcg gggctgtgcc ttttactgct    2880
gctggaaggg ggtggtgtgt cgccccaaaa gcagggcttc aattaagaaa tgcctctttg    2940
aaaggtgtac cttgggtatc ctgtctgagg gtaactccag ggtgcgccac aatgtggcct    3000
ccgactgtgg ttgcttcatg ctagtgaaaa gcgtggctgt gattaagcat aacatggtat    3060
gtggcaactg cgaggacagg gcctctcaga tgctgacctg ctcggacggc aactgtcacc    3120
tgctgaagac cattcacgta gccagccact ctcgcaaggc ctggccagtg tttgagcata    3180
acatactgac ccgctgttcc ttgcatttgg gtaacaggag ggggtgttc ctaccttacc    3240 aatgcaattt gagtcacact aagatattgc ttgagcccga gagcatgtcc aaggtgaacc    3300
tgaacggggt gtttgacatg accatgaaga tctggaaggt gctgaggtac gatgagaccc    3360
gcaccaggtg cagaccctgc gagtgtggcg gtaaacatat taggaaccag cctgtgatgc    3420
tggatgtgac cgaggagctg aggcccgatc acttggtgct ggcctgcacc cgcgctgagt    3480
ttggctctag cgatgaagat acagattgag gtactgaaat gtgtgggcgt ggcttaaggg    3540
tgggaaagaa tatataaggt gggggtctta tgtagttttg tatctgtttt gcagcagccg    3600
ccgccgccat gagcaccaac tcgtttgatg gaagcattgt gagctcatat ttgacaacgc    3660
gcatgccccc atgggccggg gtgcgtcaga atgtgatggg ctccagcatt gatggtcgcc    3720
ccgtcctgcc cgcaaactct actaccttga cctacgagac cgtgtctgga acgccgttgg    3780
agactgcagc ctccgccgcc gcttcagccg ctgcagccac cgcccgcggg attgtgactg    3840
actttgcttt cctgagcccg cttgcaagca gtgcagcttc ccgttcatcc gcccgcgatg    3900
acaagttgac ggctcttttg gcacaattgg attctttgac ccgggaactt aatgtcgttt    3960
ctcagcagct gttggatctg cgccagcagg tttctgccct gaaggcttcc tcccctccca    4020
atgcggttta aaacataaat aaaaaaccag actctgtttg gatttggatc aagcaagtgt    4080
cttgctgtct ttatttaggg gttttgcgcg cgcggtaggc ccgggaccag cggtctcggt    4140
cgttgagggt cctgtgtatt ttttccagga cgtggtaaag gtgactctgg atgttcagat    4200
acatgggcat aagcccgtct ctggggtgga ggtagcacca ctgcagagct tcatgctgcg    4260
gggtggtgtt gtagatgatc cagtcgtagc aggagcgctg ggcgtggtgc ctaaaaatgt    4320 cttttcagtag caagctgatt gccaggggca ggcccttggt gtaagtgttt acaaagcggt    4380
taagctggga tgggtgcata cgtggggata tgagatgcat cttggactgt attttttaggt    4440 tggctatgtt cccagccata tccctccggg gattcatgtt gtgcagaacc accagcacag    4500
tgtatccggt gcacttggga aatttgtcat gtagcttaga aggaaatgcg tggaagaact    4560
tggagacgcc cttgtgacct ccaagatttt ccatgcattc gtccataatg atggcaatgg    4620
gcccacgggc ggcggcctgg gcgaagatat ttctgggatc actaacgtca tagttgtgtt    4680
ccaggatgag atcgtcatag gccattttta caaagcgcgg gcgagggtg ccagactgcg    4740 gtataatggt tccatccggc ccaggggcgt agttaccctc acagatttgc atttcccacg    4800
ctttgagttc agatgggggg atcatgtcta cctgcggggc gatgaagaaa acggtttccg    4860
gggtagggga gatcagctgg gaagaaagca ggttcctgag cagctgcgac ttaccgcagc    4920
cggtgggccc gtaaatcaca cctattaccg ggtgcaactg gtagttaaga gagctgcagc    4980
tgccgtcatc cctgagcagg ggggccactt cgttaagcat gtccctgact cgcatgtttt    5040
ccctgaccaa atccgccaga aggcgctcgc cgcccagcga tagcagttct tgcaaggaag    5100
```

```
caaagttttt caacggtttg agaccgtccg ccgtaggcat gcttttgagc gtttgaccaa    5160
gcagttccag gcggtcccac agctcggtca cctgctctac ggcatctcga tccagcatat    5220
ctcctcgttt cgcgggttgg ggcggctttc gctgtacggc agtagtcggt gctcgtccag    5280
acgggccagg gtcatgtctt tccacgggcg cagggtcctc gtcagcgtag tctgggtcac    5340
ggtgaagggg tgcgctccgg gctgcgcgct ggccagggtg cgcttgaggc tggtcctgct    5400
ggtgctgaag cgctgccggt cttcgccctg cgcgtcggcc aggtagcatt tgaccatggt    5460
gtcatagtcc agcccctccg cggcgtggcc cttggcgcgc agcttgccct ggaggaggc     5520
gccgcacgag gggcagtgca gacttttgag ggcgtagagc ttgggcgcga gaataccga     5580
ttccggggag taggcatccg cgccgcaggc cccgcagacg gtctcgcatt ccacgagcca    5640
ggtgagctct ggccgttcgg ggtcaaaaac caggtttccc ccatgctttt tgatgcgttt    5700
cttacctctg gtttccatga gccggtgtcc acgctcggtg acgaaaaggc tgtccgtgtc    5760
cccgtataca gacttgagag gcctgtcctc gagcggtgtt ccgcggtcct cctcgtatag    5820
aaactcggac cactctgaga caaaggctcg cgtccaggcc agcacgaagg aggctaagtg    5880
ggaggggtag cggtcgttgt ccactagggg gtccactcgc tccagggtgt gaagacacat    5940
gtcgccctct tcggcatcaa ggaaggtgat tggtttgtag gtgtaggcca cgtgaccggg    6000
tgttcctgaa gggggctat aaagggggt ggggcgcgt tcgtcctcac tctcttccgc      6060
atcgctgtct gcgagggcca gctgttgggg tgagtactcc ctctgaaaag cgggcatgac    6120
ttctgcgcta agattgtcag tttccaaaaa cgaggaggat tgatattca cctggcccgc     6180
ggtgatgcct ttgagggtgg ccgcatccat ctggtcagaa aagacaatct ttttgttgtc    6240
aagcttggtg gcaaacgacc cgtagagggc gttggacagc aacttggcga tggagcgcag    6300
ggtttggttt ttgtcgcgat cggcgcgctc cttggccgcg atgtttagct gcacgtattc    6360
gcgcgcaacg caccgccatt cgggaaagac ggtggtgcgc tcgtcgggca ccaggtgcac    6420
gcgccaaccg cggttgtgca gggtgacaag gtcaacgctg gtggctacct ctccgcgtag    6480
gcgctcgttg gtccagcaga ggcggccgcc cttgcgcgag cagaatggcg gtaggggtc     6540
tagctgcgtc tcgtccgggg ggtctgcgtc cacggtaaag accccgggca gcaggcgcgc    6600
gtcgaagtag tctatcttgc atccttgcaa gtctagcgcc tgctgccatg cgcgggcggc    6660
aagcgcgcgc tcgtatgggt tgagtggggg accccatggc atgggtggg tgagcgcgga    6720
ggcgtacatg ccgcaaatgt cgtaaacgta gaggggctct ctgagtattc caagatatgt    6780
agggtagcat cttccaccgc ggatgctggc gcgcacgtaa tcgtatagtt cgtgcgaggg    6840
agcgaggagg tcgggaccga ggttgctacg ggcgggctgc tctgctcgga agactatctg    6900
cctgaagatg gcatgtgagt tggatgatat ggttggacgc tggaagacgt tgaagctggc    6960
gtctgtgaga cctaccgcgt cacgcacgaa ggaggcgtag gagtcgcgca gcttgttgac    7020
cagctcggcg gtgacctgca cgtctagggc gcagtagtcc agggtttcct tgatgatgtc    7080
atacttatcc tgtccctttt ttttccacag ctcgcggttg aggacaaact cttcgcggtc    7140
tttccagtac tcttggatcg gaaacccgtc ggcctccgaa cggtaagagc ctagcatgta    7200
gaactggttg acgcctggt aggcgcagca tccctttct acgggtagcg cgtatgcctg     7260
cgcggccttc cggagcgagg tgtgggtgag cgcaaaggtg tccctgacca tgactttgag    7320
gtactggtat ttgaagtcag tgtcgtcgca tccgccctgc tcccagagca aaaagtccgt    7380
gcgcttttg aacgcggat ttggcagggc gaaggtgaca tcgttgaaga gtatctttcc      7440
cgcgcgaggc ataaagttgc gtgtgatgcg gaagggtccc ggcacctcgg aacggttgtt    7500
```

```
aattacctgg gcggcgagca cgatctcgtc aaagccgttg atgttgtggc ccacaatgta    7560
aagttccaag aagcgcggga tgcccttgat ggaaggcaat tttttaagtt cctcgtaggt    7620
gagctcttca ggggagctga gcccgtgctc tgaaagggcc cagtctgcaa gatgagggtt    7680
ggaagcgacg aatgagctcc acaggtcacg ggccattagc atttgcaggt ggtcgcgaaa    7740
ggtcctaaac tggcgaccta tggccatttt ttctggggtg atgcagtaga aggtaagcgg    7800
gtcttgttcc cagcggtccc atccaaggtt cgcggctagg tctcgcgcgg cagtcactag    7860
aggctcatct ccgccgaact tcatgaccag catgaagggc acgagctgct tcccaaaggc    7920
ccccatccaa gtataggtct ctacatcgta ggtgacaaag agacgctcgg tgcgaggatg    7980
cgagccgatc gggaagaact ggatctcccg ccaccaattg gaggagtggc tattgatgtg    8040
gtgaaagtag aagtccctgc gacgggccga acactcgtgc tggcttttgt aaaaacgtgc    8100
gcagtactgg cagcggtgca cgggctgtac atcctgcacg aggttgacct gacgaccgcg    8160
cacaaggaag cagagtggga atttgagccc ctcgcctggc gggtttggct ggtggtcttc    8220
tacttcggct gcttgtcctt gaccgtctgg ctgctcgagg ggagttacgg tggatcggac    8280
caccacgccg cgcgagccca aagtccagat gtccgcgcgc ggcggtcgga gcttgatgac    8340
aacatcgcgc agatgggagc tgtccatggt ctggagctcc cgcggcgtca ggtcaggcgg    8400
gagctcctgc aggtttacct cgcatagacg ggtcagggcg cgggctagat ccaggtgata    8460
cctaatttcc aggggctggt tggtggcggc gtcgatggct tgcaagaggc cgcatccccg    8520
cggcgcgact acggtaccgc gcggcgggcg gtgggccgcg ggggtgtcct tggatgatgc    8580
atctaaaagc ggtgacgcgg gcgagccccc ggaggtaggg ggggctccgg acccgccggg    8640 agaggggca ggggcacgtc ggccgccgcg cgggcagga gctggtgctg cgcgcgtagg    8700
ttgctggcga acgcgacgac gcggcggttg atctcctgaa tctggcgcct ctgcgtgaag    8760
acgacgggcc cggtgagctt gagcctgaaa gagagttcga cagaatcaat ttcggtgtcg    8820
ttgacggcgg cctggcgcaa aatctcctgc acgtctcctg agttgtcttg ataggcgatc    8880
tcggccatga actgctcgat ctcttcctcc tggagatctc cgcgtccggc tcgctccacg    8940
gtggcggcga ggtcgttgga aatgcgggcc atgagctgcg agaaggcgtt gaggcctccc    9000
tcgttccaga cgcggctgta gaccacgccc ccttcggcat cgcgggcgcg catgaccacc    9060
tgcgcgagat tgagctccac gtgccgggcg aagacgcgt agtttcgcag cgcgctgaaag    9120 aggtagttga gggtggtggc ggtgtgttct gccacgaaga agtacataac ccagcgtcgc    9180
aacgtggatt cgttgatatc ccccaaggcc tcaaggcgct ccatggcctc gtagaagtcc    9240
acggcgaagt tgaaaaactg ggagttgcgc ccgacacgg ttaactcctc ctccagaaga    9300
cggatgagct cggcgacagt gtcgcgcacc tcgcgctcaa aggctacagg ggcctcttct    9360
tcttcttcaa tctcctcttc cataagggcc tccccttctt cttcttctgg cggcggtggg    9420 ggaggggga cacggcggcg acgacggcgc accgggaggc ggtcgacaaa gcgctcgatc    9480
atctccccgc ggcgacggcg catggtctcg gtgacggcgc ggccgttctc gcggggcgc    9540 agttggaaga cgccgcccgt catgtcccgg ttatgggttg cgggggggct gccatgcggc    9600
agggatacgg cgctaacgat gcatctcaac aattgttgtg taggtactcc gccgccgagg    9660
gacctgagcg agtccgcatc gaccggatcg gaaaacctct cgagaaaggc gtctaaccag    9720
tcacagtcgc aaggtaggct gagcaccgtg gcggcggca gcgggcggcg gtcgggttg    9780 tttctggcgg aggtgctgct gatgatgtaa ttaaagtagg cggtcttgag acggcggatg    9840
```

-continued

```
gtcgacagaa gcaccatgtc cttgggtccg gcctgctgaa tgcgcaggcg gtcggccatg    9900
ccccaggctt cgttttgaca tcggcgcagg tctttgtagt agtcttgcat gagcctttct    9960
accggcactt cttcttctcc ttcctcttgt cctgcatctc ttgcatctat cgctgcggcg   10020
gcggcggagt ttggccgtag gtggcgccct cttcctccca tgcgtgtgac cccgaagccc   10080
ctcatcggct gaagcagggc taggtcggcg acaacgcgct cggctaatat ggcctgctgc   10140
acctgcgtga gggtagactg gaagtcatcc atgtccacaa gcggtggta tgcgcccgtg    10200 ttgatggtgt aagtgcagtt ggccataacg gaccagttaa cggtctggtg acccggctgc   10260
gagagctcgg tgtacctgag acgcgagtaa gccctcgagt caaatacgta gtcgttgcaa   10320
gtccgcacca ggtactggta tcccaccaaa aagtgcggcg gcggctggcg gtagaggggc   10380
cagcgtaggg tggccgggc tccggggcg agatcttcca acataaggcg atgatatccg     10440
tagatgtacc tggacatcca ggtgatgccg gcggcggtgg tggaggcgcg cggaaagtcg   10500
cggacgcggt tccagatgtt gcgcagcggc aaaaagtgct ccatggtcgg gacgctctgg   10560
ccggtcaggc gcgcgcaatc gttgacgctc tagaccgtgc aaaaggagag cctgtaagcg   10620
ggcactcttc cgtggtctgg tggataaatt cgcaagggta tcatggcgga cgaccggggt   10680
tcgagccccg tatccggccg tccgccgtga tccatgcggt taccgcccgc gtgtcgaacc   10740
caggtgtgcg acgtcagaca acgggggagt gctccttttg gcttccttcc aggcgcggcg   10800
gctgctgcgc tagcttttt ggccactggc cgcgcgcagc gtaagcggtt aggctggaaa    10860
gcgaaagcat taagtggctc gctccctgta gccggagggt tattttccaa gggttgagtc   10920
gcgggacccc cggttcgagt ctcggaccgg ccggactgcg gcgaacgggg gtttgcctcc   10980
ccgtcatgca agacccgct tgcaaattcc tccggaaaca gggacgagcc ccttttttgc    11040
ttttcccaga tgcatccggt gctgcggcag atgcgccccc ctcctcagca gcggcaagag   11100
caagagcagc ggcagacatg cagggcaccc tcccctcctc ctaccgcgtc aggagggcg    11160 acatccgcgg ttgacgcggc agcagatggt gattacgaac ccccgcggcg ccgggcccgg   11220
cactacctgg acttggagga gggcgagggc ctggcgcggc taggagcgcc ctctcctgag   11280
cggtacccaa gggtgcagct gaagcgtgat acgcgtgagg cgtacgtgcc gcggcagaac   11340
ctgtttcgcg accgcgaggg agaggagccc gaggagatgc gggatcgaaa gttccacgca   11400
gggcgcgagc tgcggcatgg cctgaatcgc gagcggttgc tgcgcgagga ggactttgag   11460
cccgacgcgc gaaccgggat tagtcccgcg cgcgcacacg tggcggccgc cgacctggta   11520
accgcatacg agcagacggt gaaccaggag attaactttc aaaaaagctt taacaaccac   11580
gtgcgtacgc ttgtggcgcg cgaggaggtg gctataggac tgatgcatct gtgggacttt   11640
gtaagcgcgc tggagcaaaa cccaaatagc aagccgctca tggcgcagct gttccttata   11700
gtgcagcaca gcagggacaa cgaggcattc agggatgcgc tgctaaacat agtagagccc   11760
gagggccgct ggctgctcga tttgataaac atcctgcaga gcatagtggt gcaggagcgc   11820
agcttgagcc tggctgacaa ggtggccgcc atcaactatt ccatgcttag cctgggcaag   11880
ttttacgccc gcaagatata ccataccct tacgttccca tagacaagga ggtaaagatc     11940
gaggggttct acatgcgcat ggcgctgaag gtgcttacct tgagcgacga cctgggcgtt   12000
tatcgcaacg agcgcatcca caaggccgtg agcgtgagcc ggcggcgcga gctcagcgac   12060
cgcgagctga tgcacagcct gcaaagggc ctggctggca cgggcagcgg cgatagagag    12120
gccgagtcct actttgacgc gggcgctgac ctgcgctggg cccaagccg acgcgccctg    12180 gaggcagctg gggccggacc tgggctggcg gtggcacccg cgcgcgctgg caacgtcggc   12240
```

-continued

```
ggcgtggagg aatatgacga ggacgatgag tacgagccag aggacggcga gtactaagcg    12300
gtgatgtttc tgatcagatg atgcaagacg caacggaccc ggcggtgcgg gcggcgctgc    12360
agagccagcc gtccggcctt aactccacgg acgactggcg ccaggtcatg gaccgcatca    12420
tgtcgctgac tgcgcgcaat cctgacgcgt tccggcagca gccgcaggcc aaccggctct    12480
ccgcaattct ggaagcggtg gtcccggcgc gcgcaaaccc cacgcacgag aaggtgctgg    12540
cgatcgtaaa cgcgctggcc gaaaacaggg ccatccggcc cgacgaggcc ggcctggtct    12600
acgacgcgct gcttcagcgc gtggctcgtt acaacagcgg caacgtgcag accaacctgg    12660
accggctggt gggggatgtg cgcgaggccg tggcgcagcg tgagcgcgcg cagcagcagg    12720
gcaacctggg ctccatggtt gcactaaacg ccttcctgag tacacagccc gccaacgtgc    12780
cgcggggaca ggaggactac accaactttg tgagcgcact gcggctaatg gtgactgaga    12840
caccgcaaag tgaggtgtac cagtctgggc cagactattt tttccagacc agtagacaag    12900
gcctgcagac cgtaaacctg agccaggctt tcaaaaactt gcaggggctg tggggggtgc    12960
gggctcccac aggcgaccgc gcgaccgtgt ctagcttgct gacgcccaac tcgcgcctgt    13020
tgctgctgct aatagcgccc ttcacggaca gtggcagcgt gtcccgggac acatacctag    13080
gtcacttgct gacactgtac cgcgaggcca taggtcaggc gcatgtggac gagcatactt    13140
tccaggagat tacaagtgtc agccgcgcgc tggggcagga ggacacgggc agcctggagg    13200
caaccctaaa ctacctgctg accaaccggc ggcagaagat ccccctcgttg cacagtttaa    13260 acagcgagga ggagcgcatt ttgcgctacg tgcagcagag cgtgagccct aacctgatgc    13320
gcgacggggt aacgcccagc gtggcgctgg acatgaccgc gcgcaacatg gaaccgggca    13380
tgtatgcctc aaaccggccg tttatcaacc gcctaatgga ctacttgcat cgcgcggccg    13440
ccgtgaaccc cgagtatttc accaatgcca tcttgaaccc gcactggcta ccgcccctg    13500 gtttctacac cggggattc gaggtgcccg agggtaacga tggattcctc tgggacgaca    13560
tagacgacag cgtgtttcc ccgcaaccgc agaccctgct agagttgcaa cagcgcgagc    13620
aggcagaggc ggcgctgcga aaggaaagct tccgcaggcc aagcagcttg tccgatctag    13680
gcgctgcggc cccgcggtca gatgctagta gcccatttcc aagcttgata gggtctctta    13740
ccagcactcg caccacccgc ccgcgcctgc tgggcgagga ggagtaccta aacaactcgc    13800
tgctgcagcc gcagcgcgaa aaaaacctgc ctccggcatt tcccaacaac gggatagaga    13860
gcctagtgga caagatgagt agatggaaga cgtacgcgca ggagcacagg gacgtgccag    13920
gccccgcgcc gcccacccgt cgtcaaaggc acgaccgtca gcggggtctg gtgtgggagg    13980
acgatgactc ggcagacgac agcagcgtcc tggatttggg agggagtggc aacccgtttg    14040
cgcaccttcg ccccaggctg gggagaatgt tttaaaaaaa aaaagcatg atgcaaaata    14100 aaaaactcac caaggccatg gcaccgagcg ttggttttct tgtattcccc ttagtatgcg    14160
gcgcgcggcg atgtatgagg aaggtcctcc tccctcctac gagagtgtgg tgagcgcggc    14220
gccagtggcg gcggcgctgg gttctccctt cgatgctccc ctggaccgc cgtttgtgcc    14280 tccgcggtac ctgcggccta ccgggggag aaacagcatc cgttactctg agttggcacc    14340
cctattcgac accaccgtg tgtacctggt ggacaacaag tcaacggatg tggcatccct    14400
gaactaccag aacgaccaca gcaactttct gaccacggtc attcaaaaca atgactacag    14460
cccgggggag gcaagcacac agaccatcaa tcttgacgac cggtcgcact ggggcggcga    14520
cctgaaaacc atcctgcata ccaacatgcc aaatgtgaac gagttcatgt ttaccaataa    14580
```

```
gtttaaggcg cgggtgatgg tgtcgcgctt gcctactaag gacaatcagg tggagctgaa    14640
atacgagtgg gtggagttca cgctgcccga gggcaactac tccgagacca tgaccataga    14700
ccttatgaac aacgcgatcg tggagcacta cttgaaagtg ggcagacaga acggggttct    14760
ggaaagcgac atcggggtaa agtttgacac ccgcaacttc agactggggt ttgaccccgt    14820
cactggtctt gtcatgcctg ggtatatac  aaacgaagcc ttccatccag acatcatttt    14880
gctgccagga tgcggggtgg acttcaccca cagccgcctg agcaacttgt tgggcatccg    14940
caagcggcaa cccttccagg agggctttag gatcacctac gatgatctgg agggtggtaa    15000
cattcccgca ctgttggatg tggacgccta ccaggcgagc ttgaaagatg acaccgaaca    15060 gggcggggt  ggcgcaggcg gcagcaacag cagtggcagc ggcgcggaag agaactccaa    15120
cgcggcagcc gcggcaatgc agccggtgga ggacatgaac gatcatgcca ttcgcggcga    15180 caccttgcc  acacgggctg aggagaagcg cgctgaggcc gaagcagcgg ccgaagctgc    15240
cgcccccgct gcgcaacccg aggtcgagaa gcctcagaag aaaccggtga tcaaacccct    15300
gacagaggac agcaagaaac gcagttacaa cctaataagc aatgacagca ccttcaccca    15360
gtaccgcagc tggtaccttg catacaacta cggcgaccct cagaccggaa tccgctcatg    15420
gaccctgctt tgcactcctg acgtaacctg cggctcggag caggtctact ggtcgttgcc    15480
agacatgatg caagaccccg tgaccttccg ctccacgcgc cagatcagca actttccggt    15540
ggtgggcgcc gagctgttgc ccgtgcactc caagagcttc tacaacgacc aggccgtcta    15600
ctcccaactc atccgccagt ttacctctct gacccacgtg ttcaatcgct ttcccgagaa    15660
ccagattttg gcgcgcccgc cagccccac  catcaccacc gtcagtgaaa cgttcctgc     15720 tctcacagat cacgggacgc taccgctgcg caacagcatc ggaggagtcc agcgagtgac    15780
cattactgac gccagacgcc gcacctgccc ctacgtttac aaggccctgg gcatagtctc    15840
gccgcgcgtc ctatcgagcc gcactttttg agcaagcatg tccatcctta tatcgcccag    15900
caataacaca ggctggggcc tgcgcttccc aagcaagatg tttggcgggg ccaagaagcg    15960
ctccgaccaa cacccagtgc gcgtgcgcgg gcactaccgc gcgccctggg gcgcgcacaa    16020
acgcggccgc actgggcgca ccaccgtcga tgacgccatc gacgcggtgg tggaggaggc    16080
gcgcaactac acgcccacgc cgccaccagt gtccacagtg gacgcggcca ttcagaccgt    16140
ggtgcgcgga gcccggcgct atgctaaaat gaagagacgg cggaggcgcg tagcacgtcg    16200
ccaccgccgc cgacccggca ctgccgccca acgcgcggcg gcggccctgc ttaaccgcgc    16260
acgtcgcacc ggccgacggg cggccatgcg ggccgctcga aggctggccg cgggtattgt    16320
cactgtgccc cccaggtcca ggcgacgagc ggccgccgca gcagccgcgg ccattagtgc    16380
tatgactcag ggtcgcaggg gcaacgtgta ttgggtgcgc gactcggtta gcggcctgcg    16440
cgtgcccgtg cgcacccgcc ccccgcgcaa ctagattgca agaaaaaact acttagactc    16500
gtactgttgt atgtatccag cggcggcggc gcgcaacgaa gctatgtcca agcgcaaaat    16560
caaagaagag atgctccagg tcatcgcgcc ggagatctat ggccccccga agaaggaaga    16620
gcaggattac aagccccgaa agctaaagcg ggtcaaaaag aaaagaaag  atgatgatga    16680 tgaacttgac gacgaggtgg aactgctgca cgctaccgcg cccaggcgac gggtacagtg    16740
gaaaggtcga cgcgtaaaac gtgttttgcg accggcacc  accgtagtct ttacgcccgg    16800
tgagcgctcc acccgcacct acaagcgcgt gtatgatgag gtgtacgcg  acgaggacct    16860 gcttgagcag gccaacgagc gcctcgggga gtttgcctac ggaaagcggc ataaggacat    16920
gctggcgttg ccgctggacg agggcaaccc aacacctagc ctaaagcccg taacactgca    16980
```

```
gcaggtgctg cccgcgcttg caccgtccga agaaaagcgc ggcctaaagc gcgagtctgg    17040
tgacttggca cccaccgtgc agctgatggt acccaagcgc agcgactgg aagatgtctt    17100 ggaaaaaatg accgtggaac ctgggctgga gcccgaggtc cgcgtgcggc caatcaagca    17160
ggtggcgccg ggactgggcg tgcagaccgt ggacgttcag atacccacta ccagtagcac    17220
cagtattgcc accgccacag agggcatgga gacacaaacg tccccggttg cctcagcggt    17280
ggcggatgcc gcggtgcagg cggtcgctgc ggccgcgtcc aagacctcta cggaggtgca    17340
aacggacccg tggatgtttc gcgtttcagc cccccggcgc ccgcgcggtt cgaggaagta    17400
cggcgccgcc agcgcgctac tgcccgaata tgccctacat ccttccattg cgcctacccc    17460
cggctatcgt ggctacacct accgcccag aagacgagca actacccgac gccgaaccac    17520
cactggaacc cgccgccgcc gtcgccgtcg ccagcccgtg ctggcccga tttccgtgcg    17580 cagggtggct cgcgaaggag gcaggaccct ggtgctgcca acagcgcgct accaccccag    17640
catcgtttaa aagccggtct ttgtggttct tgcagatatg ccctcacct gccgcctccg    17700 tttcccggtg ccgggattcc gaggaagaat gcaccgtagg aggggcatgg ccggccacgg    17760
cctgacgggc ggcatgcgtc gtgcgcacca ccggcggcgg cgcgcgtcgc accgtcgcat    17820
gcgcggcggt atcctgcccc tccttattcc actgatcgcc gcggcgattg gcgccgtgcc    17880
cggaattgca tccgtggcct tgcaggcgca gagacactga ttaaaaacaa gttgcatgtg    17940 gaaaatcaa aataaaaagt ctggactctc acgctcgctt ggtcctgtaa ctattttgta    18000
gaatggaaga catcaacttt gcgtctctgg ccccgcgaca cggctcgcgc ccgttcatgg    18060
gaaactggca agatatcggc accagcaata tgagcggtgg cgccttcagc tggggctcgc    18120
tgtggagcgg cattaaaaat ttcggttcca ccgttaagaa ctatggcagc aaggcctgga    18180
acagcagcac aggccagatg ctgagggata agttgaaaga gcaaaatttc caacaaaagg    18240
tggtagatgg cctggcctct ggcattagcg gggtggtgga cctggccaac caggcagtgc    18300
aaaataagat taacagtaag cttgatcccc gccctcccgt agaggagcct ccaccggccg    18360
tggagacagt gtctccagag gggcgtggcg aaaagcgtcc gcgccccgac agggaagaaa    18420
ctctggtgac gcaaatagac gagcctccct cgtacgagga ggcactaaag caaggcctgc    18480
ccaccacccg tcccatcgcg cccatggcta ccggagtgct gggccagcac acacccgtaa    18540
cgctggacct gcctcccccc gccgacaccc agcagaaacc tgtgctgcca ggcccgaccg    18600
ccgttgttgt aacccgtcct agccgcgcgt ccctgcgccg cgccgccagc ggtccgcgat    18660
cgttgcggcc cgtagccagt ggcaactggc aaagcacact gaacagcatc gtgggtctgg    18720
gggtgcaatc cctgaagcgc cgacgatgct tctgaatagc taacgtgtcg tatgtgtgtc    18780
atgtatgcgt ccatgtcgcc gccagaggag ctgctgagcc gccgcgcgcc cgcttttcaa    18840
gatggctacc ccttcgatga tgccgcagtg gtcttacatg cacatctcgg gccaggacgc    18900
ctcggagtac ctgagcccg ggctggtgca gtttgcccgc gccaccgaga cgtacttcag    18960
cctgaataac aagtttagaa accccacggt ggcgcctacg cacgacgtga ccacagaccg    19020
gtcccagcgt ttgacgctgc ggttcatccc tgtggaccgt gaggatactg cgtactcgta    19080
caaggcgcgg ttcacccag ctgtgggtga taacgtgtg ctggacatgg cttccacgta    19140
ctttgacatc cgcggcgtgc tggacagggg ccctacttt aagccctact ctggcactgc    19200
ctacaacgcc ctggctccca agggtgcccc aaatccttgc gaatgggatg aagctgctac    19260
tgctcttgaa ataaacctag aagaaggagg cgatgacaac gaagacgaag tagacgagca    19320
```

```
agctgagcag caaaaaactc acgtatttgg gcaggcgcct tattctggta taaatattac   19380
aaaggagggt attcaaatag gtgtcgaagg tcaaacacct aaatatgccg ataaaacatt   19440
tcaacctgaa cctcaaatag gagaatctca gtggtacgaa actgaaatta atcatgcagc   19500
tgggagagtc cttaaaaaga ctaccccaat gaaaccatgt tacggttcat atgcaaaacc   19560
cacaaatgaa aatggagggc aaggcattct tgtaaagcaa caaatggaa agctagaaag   19620 tcaagtggaa atgcaatttt tctcaactac tgaggcgacc gcaggcaatg gtgataactt   19680
gactcctaaa gtggtattgt acagtgaaga tgtagatata gaaacccag acactcatat   19740 ttcttacatg cccactatta aggaaggtaa ctcacgagaa ctaatgggcc aacaatctat   19800
gcccaacagg cctaattaca ttgcttttag ggacaatttt attggtctaa tgtattacaa   19860
cagcacgggt aatatgggtg ttctggcggg ccaagcatcg cagttgaatg ctgttgtaga   19920
tttgcaagac agaaacacag agctttcata ccagcttttg cttgattcca ttggtgatag   19980
aaccaggtac ttttctatgt ggaatcaggc tgttgacagc tatgatccag atgttagaat   20040
tattgaaaat catggaactg aagatgaact tccaaattac tgctttccac tgggaggtgt   20100
gattaataca gagactctta ccaaggtaaa acctaaaaca ggtcaggaaa atggatggga   20160
aaaagatgct acagaatttt cagataaaaa tgaaataaga gttggaaata attttgccat   20220
ggaaatcaat ctaaatgcca acctgtggag aaatttcctg tactccaaca tagcgctgta   20280
tttgcccgac aagctaaagt acagtccttc caacgtaaaa atttctgata acccaaacac   20340
ctacgactac atgaacaagc gagtggtggc tcccgggtta gtggactgct acattaacct   20400
tggagcacgc tggtcccttg actatatgga caacgtcaac ccatttaacc accaccgcaa   20460
tgctggcctg cgctaccgct caatgttgct gggcaatggt cgctatgtgc ccttccacat   20520
ccaggtgcct cagaagttct tgccattaa aaacctcctt ctcctgccgg gctcatacac   20580
ctacgagtgg aacttcagga aggatgttaa catggttctg cagagctccc taggaaatga   20640
cctaagggtt gacggagcca gcattaagtt tgatagcatt tgcctttacg ccaccttctt   20700
ccccatggcc cacaacaccg cctccacgct tgaggccatg cttagaaacg acaccaacga   20760
ccagtccttt aacgactatc tctccgccgc caacatgctc tacccatac ccgccaacgc   20820 taccaacgtg cccatatcca tcccctcccg caactgggcg ctttccgcg ctgggcctt   20880 cacgcgcctt aagactaagg aaacccatc actgggctcg ggctacgacc cttattacac   20940
ctactctggc tctataccct acctagatgg aaccttttac ctcaaccaca cctttaagaa   21000
ggtggccatt acctttgact cttctgtcag ctggcctggc aatgaccgcc tgcttacccc   21060
caacgagttt gaaattaagc gctcagttga cggggagggt tacaacgttg cccagtgtaa   21120
catgaccaaa gactggttcc tggtacaaat gctagctaac tacaacattg gctaccaggg   21180
cttctatatc ccagagagct acaaggaccg catgtactcc ttctttagaa acttccagcc   21240
catgagccgt caggtggtgg atgatactaa atacaaggac taccaacagg tgggcatcct   21300
acaccaacac aacaactctg gatttgttgg ctaccttgcc cccaccatgc gcgaaggaca   21360
ggcctaccct gctaacttcc cctatccgct tataggcaag accgcagttg acagcattac   21420
ccagaaaaag tttctttgcg atcgcaccct ttggcgcatc ccattctcca gtaacttat   21480 gtccatgggc gcactcacag acctgggcca aaaccttctc tacgccaact ccgcccacgc   21540
gctagacatg acttttgagg tggatccat ggacgagccc acccttcttt atgttttgtt   21600
tgaagtcttt gacgtggtcc gtgtgcaccg gccgcaccgc ggcgtcatcg aaaccgtgta   21660
cctgcgcacg cccttctcgg ccggcaacgc cacaacataa agaagcaagc aacatcaaca   21720
```

```
acagctgccg ccatgggctc cagtgagcag gaactgaaag ccattgtcaa agatcttggt  21780
tgtgggccat attttttggg cacctatgac aagcgctttc caggctttgt ttctccacac  21840
aagctcgcct gcgccatagt caatacggcc ggtcgcgaga ctgggggcgt acactggatg  21900
gcctttgcct ggaacccgca ctcaaaaaca tgctacctct ttgagccctt tggcttttct  21960
gaccagcgac tcaagcaggt ttaccagttt gagtacgagt cactcctgcg ccgtagcgcc  22020
attgcttctt cccccgaccg ctgtataacg ctggaaaagt ccacccaaag cgtacagggg  22080
cccaactcgg ccgcctgtgg actattctgc tgcatgtttc tccacgcctt tgccaactgg  22140
ccccaaactc ccatggatca caaccccacc atgaaccttaa ttaccggggt acccaactcc  22200
atgctcaaca gtccccaggt acagcccacc ctgcgtcgca accaggaaca gctctacagc  22260
ttcctggagc gccactcgcc ctacttccgc agccacagtg cgcagattag gagcgccact  22320
tcttttttgtc acttgaaaaa catgtaaaaa taatgtacta gagacactttt caataaaggc  22380
aaatgctttt atttgtacac tctcgggtga ttatttaccc ccaccccttgc cgtctgcgcc  22440
gtttaaaaat caaaggggtt ctgccgcgca tcgctatgcg ccactggcag ggacacgttg  22500
cgatactggt gtttagtgct ccacttaaac tcaggcacaa ccatccgcgg cagctcggtg  22560
aagtttttcac tccacaggct gcgcaccatc accaacgcgt ttagcaggtc gggcgccgat  22620
atcttgaagt cgcagttggg gcctccgccc tgcgcgcgcg agttgcgata cacagggttg  22680
cagcactgga acactatcag cgccgggtgg tgcacgctgg ccagcacgct cttgtcggag  22740
atcagatccg cgtccaggtc ctccgcgttg ctcaggcga acggagtcaa ctttggtagc  22800
tgccttccca aaaagggcgc gtgcccaggc tttgagttgc actcgcaccg tagtggcatc  22860
aaaaggtgac cgtgcccggt ctgggcgtta ggatacagcg cctgcataaa agccttgatc  22920
tgcttaaaag ccacctgagc cttttgcgcct tcagagaaga acatgccgca agacttgccg  22980
gaaaactgat tggccggaca ggccgcgtcg tgcacgcagc accttgcgtc ggtgttggag  23040
atctgcacca catttcggcc ccaccggttc ttcacgatct tggccttgct agactgctcc  23100
ttcagcgcgc gctgcccgtt ttcgctcgtc acatccattt caatcacgtg ctccttattt  23160
atcataatgc ttccgtgtag acacttaagc tcgccttcga tctcagcgca gcggtgcagc  23220
cacaacgcgc agcccgtggg ctcgtgatgc ttgtaggtca cctctgcaaa cgactgcagg  23280
tacgcctgca ggaatcgccc catcatcgtc acaaaggtct tgttgctggt gaaggtcagc  23340
tgcaacccgc ggtgctcctc gttcagccag gtcttgcata cggccgccag agcttccact  23400
tggtcaggca gtagtttgaa gttcgccttt agatcgttat ccacgtggta cttgtccatc  23460
agcgcgcgcg cagcctccat gcccttctcc cacgcagaca cgatcggcac actcagcggg  23520
ttcatcaccg taatttcact ttccgcttcg ctgggctctt cctcttcctc ttgcgtccgc  23580
ataccacgcg ccactgggtc gtcttcattc agccgccgca ctgtgcgctt acctcctttg  23640
ccatgcttga ttagcaccgg tgggttgctg aaacccacca tttgtagcgc cacatcttct  23700
ctttcttcct cgctgtccac gattacctct ggtgatggcg ggcgctcggg cttgggagaa  23760
gggcgcttct ttttcttctt gggcgcaatg gccaaatccg ccgccgaggt cgatggccgc  23820
gggctgggtg tgcgcggcac cagcgcgtct tgtgatgagt cttcctcgtc ctcggactcg  23880
atacgccgcc tcatccgctt ttttgggggc gcccggggag gcggcggcga cggggacggg  23940
gacgacacgt cctccatggt tggggacgt cgcgccgcac cgcgtccgcg ctcggggtgt  24000
gtttcgcgct gctcctcttc ccgactggcc atttccttct cctataggca gaaaaagatc  24060
```

```
atggagtcag tcgagaagaa ggacagccta accgcccct ctgagttcgc caccaccgcc    24120
tccaccgatg ccgccaacgc gcctaccacc ttccccgtcg aggcacccc gcttgaggag    24180 gaggaagtga ttatcgagca ggacccaggt tttgtaagcg aagacgacga ggaccgctca    24240
gtaccaacag aggataaaaa gcaagaccag gacaacgcag aggcaaacga ggaacaagtc    24300 gggcggggg acgaaaggca tggcgactac ctagatgtgg gagacgacgt gctgttgaag    24360
catctgcagc gccagtgcgc cattatctgc gacgcgttgc aagagcgcag cgatgtgccc    24420
ctcgccatag cggatgtcag ccttgcctac gaacgccacc tattctcacc gcgcgtaccc    24480
cccaaacgcc aagaaaacgg cacatgcgag cccaacccgc gcctcaactt ctacccgta   24540 tttgccgtgc cagaggtgct tgccacctat cacatctttt tccaaaactg caagatacc   24600 ctatcctgcc gtgccaaccg cagccgagcg gacaagcagc tggccttgcg gcagggcgct    24660
gtcatacctg atatcgcctc gctcaacgaa gtgccaaaaa tctttgaggg tcttggacgc    24720
gacgagaagc gcgcggcaaa cgctctgcaa caggaaaaca gcgaaaatga aagtcactct    24780
ggagtgttgg tggaactcga gggtgacaac gcgcgcctag ccgtactaaa acgcagcatc    24840
gaggtcaccc actttgccta cccggcactt aacctacccc caaggtcat gagcacagtc    24900 atgagtgagc tgatcgtgcg ccgtgcgcag cccctggaga gggatgcaaa tttgcaagaa    24960
caaacagagg agggcctacc cgcagttggc gacgagcagc tagcgcgctg gcttcaaacg    25020
cgcgagcctg ccgacttgga ggagcgacgc aaactaatga tggccgcagt gctcgttacc    25080
gtggagcttg agtgcatgca gcggttcttt gctgacccgg agatgcagcg caagctagag    25140
gaaacattgc actacacctt tcgacagggc tacgtacgcc aggcctgcaa gatctccaac    25200
gtggagctct gcaacctggt ctcctacctt ggaattttgc acgaaaaccg ccttgggcaa    25260
aacgtgcttc attccacgct caagggcgag gcgcgccgcg actacgtccg cgactgcgtt    25320
tacttatttc tatgctacac ctggcagacg gccatgggcg tttggcagca gtgcttggag    25380
gagtgcaacc tcaaggagct gcagaaactg ctaaagcaaa acttgaagga cctatggacg    25440
gccttcaacg agcgctccgt ggccgcgcac ctggcggaca tcattttccc cgaacgcctg    25500
cttaaaaccc tgcaacaggg tctgccagac ttcaccagtc aaagcatgtt gcagaacttt    25560
aggaacttta tcctagagcg ctcaggaatc ttgcccgcca cctgctgtgc acttcctagc    25620
gactttgtgc ccattaagta ccgcgaatgc cctccgccgc tttggggcca ctgctacctt    25680
ctgcagctag ccaactacct tgcctaccac tctgacataa tggaagacgt gagcggtgac    25740
ggtctactgg agtgtcactg tcgctgcaac ctatgcaccc cgcaccgctc cctggtttgc    25800
aattcgcagc tgcttaacga aagtcaaatt atcggtacct ttgagctgca gggtccctcg    25860
cctgacgaaa agtccgcggc tccgggggttg aaactcactc cggggctgtg acgtcggct    25920 taccttcgca aatttgtacc tgaggactac cacgcccacg agattaggtt ctacgaagac    25980
caatcccgcc cgccaaatgc ggagcttacc gcctgcgtca ttacccaggg ccacattctt    26040
ggccaattgc aagccatcaa caaagcccgc aagagtttc tgctacgaaa gggacggggg    26100
gtttacttgg accccagtc cggcgaggag ctcaacccaa tccccccgcc gccgcagccc    26160
tatcagcagc agccgcgggc ccttgcttcc caggatggca cccaaaaaga agctgcagct    26220
gccgccgcca cccacggacg aggaggaata ctgggacagt caggcagagg aggttttgga    26280
cgaggaggag gaggacatga tggaagactg ggagagccta gacgaggaag cttccgaggt    26340
cgaagaggtg tcagacgaaa caccgtcacc ctcggtcgca ttccctcgc cggcgcccca    26400 gaaatcggca accggttcca gcatggctac aacctccgct cctcaggcgc cgccggcact    26460
```

```
gcccgttcgc cgacccaacc gtagatggga caccactgga accagggccg gtaagtccaa   26520
gcagccgccg ccgttagccc aagagcaaca acagcgccaa ggctaccgct catggcgcgg   26580
gcacaagaac gccatagttg cttgcttgca agactgtggg ggcaacatct ccttcgcccg   26640
ccgctttctt ctctaccatc acggcgtggc cttcccccgt aacatcctgc attactaccg   26700
tcatctctac agcccatact gcaccggcgg cagcggcagc ggcagcaaca gcagcggcca   26760
cacagaagca aaggcgaccg gatagcaaga ctctgacaaa gcccaagaaa tccacagcgg   26820
cggcagcagc aggaggagga gcgctgcgtc tggcgcccaa cgaacccgta tcgacccgcg   26880
agcttagaaa caggattttt cccactctgt atgctatatt tcaacagagc aggggccaag   26940
aacaagagct gaaaataaaa aacaggtctc tgcgatccct cacccgcagc tgcctgtatc   27000
acaaaagcga agatcagctt cggcgcacgc tggaagacgc ggaggctctc ttcagtaaat   27060
actgcgcgct gactcttaag gactagtttc gcgccctttc tcaaatttaa gcgcgaaaac   27120
tacgtcatct ccagcggcca cacccggcgc cagcacctgt cgtcagcgcc attatgagca   27180
aggaaattcc cacgccctac atgtggagtt accagccaca aatgggactt gcggctggag   27240
ctgcccaaga ctactcaacc cgaataaact acatgagcgc gggaccccac atgatatccc   27300
gggtcaacgg aatccgcgcc caccgaaacc gaattctctt ggaacaggcg gctattacca   27360
ccacacctcg taataacctt aatcccgta gttggcccgc tgccctggtg taccaggaaa   27420
gtcccgctcc caccactgtg gtacttccca gagacgccca ggccgaagtt cagatgacta   27480 actcagggc gcagcttgcg gcggcttttc gtcacagggt gcggtcgccc gggcagggta   27540
taactcacct gacaatcaga gggcgaggta ttcagctcaa cgacgagtcg gtgagctcct   27600
cgcttggtct ccgtccggac gggacatttc agatcggcgg cgccggccgt ccttcattca   27660
cgcctcgtca ggcaatccta actctgcaga cctcgtcctc tgagccgcgc tctggaggca   27720
ttggaactct gcaatttatt gaggagtttg tgccatcggt ctactttaac cccttctcgg   27780
gacctcccgg ccactatccg gatcaattta ttcctaactt tgacgcggta aaggactcgg   27840
cggacggcta cgactgaatg ttaagtggag aggcagagca actgcgcctg aaacacctgg   27900
tccactgtcg ccgccacaag tgctttgccc gcgactccgg tgagttttgc tactttgaat   27960
tgcccgagga tcatatcgag ggccggcgc acggcgtccg gcttaccgcc cagggagagc   28020
ttgcccgtag cctgattcgg gagtttaccc agcgcccct gctagttgag cgggacaggg   28080
gaccctgtgt tctcactgtg atttgcaact gtcctaacct tggattacat caagatcttt   28140
gttgccatct ctgtgctgag tataataaat acagaaatta aaatatactg gggctcctat   28200
cgccatcctg taaacgccac cgtcttcacc cgcccaagca aaccaaggcg aaccttacct   28260 ggtacttta acatctctcc ctctgtgatt tacaacagtt tcaacccaga cggagtgagt   28320
ctacgagaga acctctccga gctcagctac tccatcagaa aaacaccac cctccttacc   28380 tgccgggaac gtacgagtgc gtcaccggcc gctgcaccac acctaccgcc tgaccgtaaa   28440
ccagactttt tccggacaga cctcaataac tctgtttacc agaacaggag gtgagcttag   28500 aaaccccta gggtattagg ccaaaggcgc agctactgtg gggtttatga acaattcaag   28560
caactctacg ggctattcta attcaggttt ctctagaatc ggggttgggg ttattctctg   28620
tcttgtgatt ctctttattc ttatactaac gcttctctgc ctaaggctcg ccgcctgctg   28680
tgtgcacatt tgcattttatt gtcagctttt taaacgctgg ggtcgccacc caagatgatt   28740
aggtacataa tcctaggttt actcacccttt gcgtcagccc acggtaccac ccaaaaggtg   28800
```

```
gattttaagg agccagcctg taatgttaca ttcgcagctg aagctaatga gtgcaccact    28860
cttataaaat gcaccacaga acatgaaaag ctgcttattc gccacaaaaa caaaattggc    28920
aagtatgctg tttatgctat ttggcagcca ggtgacacta cagagtataa tgttacagtt    28980
ttccagggta aaagtcataa aacttttatg tatacttttc cattttatga aatgtgcgac    29040
attaccatgt acatgagcaa acagtataag ttgtggcccc cacaaaattg tgtggaaaac    29100
actggcactt tctgctgcac tgctatgcta attacagtgc tcgctttggt ctgtacccta    29160
ctctatatta aatacaaaag cagacgcagc tttattgagg aaagaaaat gccttaattt     29220 actaagttac aaagctaatg tcaccactaa ctgctttact cgctgcttgc aaaacaaatt    29280
caaaaagtta gcattataat tagaatagga tttaaacccc ccggtcattt cctgctcaat    29340
accattcccc tgaacaattg actctatgtg ggatatgctc cagcgctaca accttgaagt    29400
caggcttcct ggatgtcagc atctgacttt ggccagcacc tgtcccgcgg atttgttcca    29460
gtccaactac agcgacccac cctaacagag atgaccaaca caaccaacgc ggccgccgct    29520
accggactta catctaccac aaatacaccc caagtttctg cctttgtcaa taactgggat    29580
aacttgggca tgtggtggtt ctccatagcg cttatgtttg tatgccttat tattatgtgg    29640
ctcatctgct gcctaaagcg caaacgcgcc cgaccaccca tctatagtcc catcattgtg    29700
ctacacccaa acaatgatgg aatccataga ttggacggac tgaaacacat gttcttttct    29760
cttacagtat gattaaatga gacatgattc ctcgagtttt tatattactg accttgttg    29820 cgcttttttg tgcgtgctcc acattggctg cggtttctca catcgaagta gactgcattc    29880
cagccttcac agtctatttg ctttacggat tgtcaccct cacgctcatc tgcagcctca    29940
tcactgtggt catcgccttt atccagtgca ttgactgggt ctgtgtgcgc tttgcatatc    30000
tcagacacca tccccagtac agggacagga ctatagctga gcttcttaga attctttaat    30060
tatgaaattt actgtgactt ttctgctgat tatttgcacc ctatctgcgt tttgttcccc    30120
gacctccaag cctcaaagac atatatcatg cagattcact cgtatatgga atattccaag    30180
ttgctacaat gaaaaagcg atctttccga agcctggtta tatgcaatca tctctgttat    30240
ggtgttctgc agtaccatct tagccctagc tatatatccc taccttgaca ttggctggaa    30300
acgaatagat gccatgaacc acccaacttt ccccgcgccc gctatgcttc cactgcaaca    30360
agttgttgcc ggcggctttg tcccagccaa tcagcctcgc cccacttctc cacccccac    30420 tgaaatcagc tactttaatc taacaggagg agatgactga caccctagat ctagaaatgg    30480
acggaattat tacagagcag cgcctgctag aaagacgcag ggcagcggcc gagcaacagc    30540
gcatgaatca agagctccaa gacatggtta acttgcacca gtgcaaaagg ggtatctttt    30600
gtctggtaaa gcaggccaaa gtcacctacg acagtaatac caccggacac cgccttagct    30660
acaagttgcc aaccaagcgt cagaaattgg tggtcatggt gggagaaaag cccattacca    30720
taactcagca ctcggtagaa accgaaggct gcattcactc accttgtcaa ggacctgagg    30780
atctctgcac ccttattaag accctgtgcg gtctcaaaga tcttattccc tttaactaat    30840
aaaaaaaaat aataaagcat cacttactta aaatcagtta gcaaatttct gtccagttta    30900
ttcagcagca cctccttgcc ctcctcccag ctctggtatt gcagcttcct cctggctgca    30960
aactttctcc acaatctaaa tggaatgtca gttttcctcct gttcctgtcc atccgcaccc    31020
actatcttca tgttgttgca gatgaagcgc gcaagaccgt ctgaagatac cttcaacccc    31080
gtgtatccat atgacacgga aaccggtcct ccaactgtgc cttttcttac tcctccctt    31140 gtatccccca atgggtttca agagagtccc cctggggtac tctctttgcg cctatccgaa    31200
```

```
cctctagtta cctccaatgg catgcttgcg ctcaaaatgg gcaacggcct ctctctggac   31260
gaggccggca accttacctc ccaaaatgta accactgtga gcccacctct caaaaaaacc   31320
aagtcaaaca taaacctgga atatctgca cccctcacag ttacctcaga agccctaact   31380
gtggctgccg ccgcacctct aatggtcgcg ggcaacacac tcaccatgca atcacaggcc   31440
ccgctaaccg tgcacgactc caaacttagc attgccaccc aaggacccct cacagtgtca   31500
gaaggaaagc tagccctgca acatcaggc cccctcacca ccaccgatag cagtacccTt   31560
actatcactg cctcaccccc tctaactact gccactggta gcttgggcat tgacttgaaa   31620
gagcccattt atacacaaaa tggaaaacta ggactaaagt acggggctcc tttgcatgta   31680
acagacgacc taaacacttt gaccgtagca actggtccag gtgtgactat taataatact   31740
tccttgcaaa ctaaagttac tggagccttg ggttttgatt cacaaggcaa tatgcaactt   31800
aatgtagcag gaggactaag gattgattct caaaacagac gccttatact tgatgttagt   31860
tatccgtttg atgctcaaaa ccaactaaat ctaagactag gacagggccc tctttttata   31920
aactcagccc acaacttgga tattaactac aacaaaggcc tttacttgtt tacagcttca   31980
aacaattcca aaaagcttga ggttaaccta agcactgcca aggggttgat gtttgacgct   32040
acagccatag ccattaatgc aggagatggg cttgaatttg gttcacctaa tgcaccaaac   32100
acaaatcccc tcaaaacaaa aattggccat ggcctagaat ttgattcaaa caaggctatg   32160
gttcctaaac taggaactgg ccttagtttt gacagcacag gtgccattac agtaggaaac   32220
aaaaataatg ataagctaac tttgtggacc acaccagctc catctcctaa ctgtagacta   32280
aatgcagaga aagatgctaa actcactttg gtcttaacaa aatgtggcag tcaaatactt   32340
gctacagttt cagttttggc tgttaaaggc agtttggctc caatatctgg aacagttcaa   32400
agtgctcatc ttattataag atttgacgaa aatggagtgc tactaaacaa ttccttcctg   32460
gacccagaat attggaactt tagaaatgga gatcttactg aaggcacagc ctatacaaac   32520
gctgttggat ttatgcctaa cctatcagct tatccaaaat ctcacggtaa aactgccaaa   32580
agtaacattg tcagtcaagt ttacttaaac ggagacaaaa ctaaacctgt aacactaacc   32640
attacactaa acggtacaca ggaaacagga gacacaactc caagtgcata ctctatgtca   32700
ttttcatggg actggtctgg ccacaactac attaatgaaa tatttgccac atcctcttac   32760 acttttttcat acattgccca agaataaaga atcgtttgtg ttatgtttca acgtgtttat   32820
ttttcaattg cagaaaattt caagtcattt ttcattcagt agtatagccc caccaccaca   32880
tagcttatac agatcaccgt accttaatca aactcacaga accctagtat tcaacctgcc   32940
acctccctcc caacacacag agtacacagt cctttctccc cggctggcct taaaaagcat   33000
catatcatgg gtaacagaca tattcttagg tgttatattc cacacggttt cctgtcgagc   33060
caaacgctca tcagtgatat taataaactc cccgggcagc tcacttaagt tcatgtcgct   33120
gtccagctgc tgagccacag gctgctgtcc aacttgcgt tgcttaacgg gcggcgaagg   33180
agaagtccac gcctacatgg gggtagagtc ataatcgtgc atcaggatag ggcggtggtg   33240
ctgcagcagc gcgcgaataa actgctgccg ccgccgctcc gtcctgcagg aatacaacat   33300
ggcagtggtc tcctcagcga tgattcgcac cgcccgcagc ataaggcgcc ttgtcctccg   33360
ggcacagcag cgcaccctga tctcacttaa atcagcacag taactgcagc acagcaccac   33420
aatattgttc aaaatcccac agtgcaaggc gctgtatcca aagctcatgg cggggaccac   33480
agaacccacg tggccatcat accacaagcg caggtagatt aagtggcgac ccctcataaa   33540
```

-continued

```
cacgctggac ataaacatta cctcttttgg catgttgtaa ttcaccacct cccggtacca   33600
tataaacctc tgattaaaca tggcgccatc caccaccatc ctaaaccagc tggccaaaac   33660
ctgcccgccg gctatacact gcagggaacc gggactggaa caatgacagt ggagagccca   33720
ggactcgtaa ccatggatca tcatgctcgt catgatatca atgttggcac aacacaggca   33780
cacgtgcata cacttcctca ggattacaag ctcctcccgc gttagaacca tatcccaggg   33840
aacaacccat tcctgaatca gcgtaaatcc cacactgcag ggaagacctc gcacgtaact   33900
cacgttgtgc attgtcaaag tgttacattc gggcagcagc ggatgatcct ccagtatggt   33960
agcgcgggtt tctgtctcaa aaggaggtag acgatcccta ctgtacggag tgcgccgaga   34020
caaccgagat cgtgttggtc gtagtgtcat gccaaatgga acgccggacg tagtcatatt   34080
tcctgaagca aaaccaggtg cgggcgtgac aaacagatct gcgtctccgg tctcgccgct   34140
tagatcgctc tgtgtagtag ttgtagtata tccactctct caaagcatcc aggcgccccc   34200
tggcttcggg ttctatgtaa actccttcat gcgccgctgc cctgataaca tccaccaccg   34260
cagaataagc cacacccagc caacctacac attcgttctg cgagtcacac acgggaggag   34320
cgggaagagc tggaagaacc atgtttttt ttttattcca aaagattatc caaaacctca   34380
aaatgaagat ctattaagtg aacgcgctcc cctccggtgg cgtggtcaaa ctctacagcc   34440
aaagaacaga taatggcatt tgtaagatgt tgcacaatgg cttccaaaag gcaaacggcc   34500
ctcacgtcca agtggacgta aaggctaaac ccttcagggt gaatctcctc tataaacatt   34560
ccagcacctt caaccatgcc caaataattc tcatctcgcc accttctcaa tatatctcta   34620
agcaaatccc gaatattaag tccggccatt gtaaaaatct gctccagagc gccctccacc   34680
ttcagcctca agcagcgaat catgattgca aaaattcagg ttcctcacag acctgtataa   34740
gattcaaaag cggaacatta acaaaaatac cgcgatcccg taggtccctt cgcagggcca   34800
gctgaacata atcgtgcagg tctgcacgga ccagcgcggc cacttccccg ccaggaacca   34860
tgacaaaaga acccacactg attatgacac gcatactcgg agctatgcta accagcgtag   34920
ccccgatgta agcttgttgc atgggcggcg atataaaatg caaggtgctg ctcaaaaaat   34980
caggcaaagc ctcgcgcaaa aaagaaagca catcgtagtc atgctcatgc agataaaggc   35040
aggtaagctc cggaaccacc acagaaaaag acaccatttt tctctcaaac atgtctgcgg   35100
gtttctgcat aaacacaaaa taaaataaca aaaaaacatt taaacattag aagcctgtct   35160
tacaacagga aaaacaaccc ttataagcat aagacggact acggccatgc cggcgtgacc   35220
gtaaaaaaac tggtcaccgt gattaaaaag caccaccgac agctcctcgg tcatgtccgg   35280
agtcataatg taagactcgg taaacacatc aggttgattc acatcggtca gtgctaaaaa   35340
gcgaccgaaa tagcccgggg gaatacatac ccgcaggcgt agagacaaca ttacagcccc   35400
cataggaggt ataacaaaat taataggaga gaaaacacaca taaacacctg aaaaaccctc   35460
ctgcctaggc aaaatagcac cctcccgctc cagaacaaca tacagcgctt ccacagcggc   35520
agccataaca gtcagcctta ccagtaaaaa agaaaaccta ttaaaaaaac accactcgac   35580
acggcaccag ctcaatcagt cacagtgtaa aaagggcca agtgcagagc gagtatatat   35640
aggactaaaa aatgacgtaa cggttaaagt ccacaaaaaa cacccagaaa accgcacgcg   35700
aacctacgcc cagaaacgaa agccaaaaaa cccacaactt cctcaaatcg tcacttccgt   35760
tttcccacgt tacgtaactt cccattttaa gaaaactaca attccaaaca catacaagtt   35820
actccgcccct aaaacctacg tcacccgccc cgttcccacg ccccgcgcca cgtcacaaac   35880
tccaccccct cattatcata ttggcttcaa tccaaaataa ggtatattat tgatgatg     35938
```

<210> SEQ ID NO 2
<211> LENGTH: 10
<212> TYPE: DNA
<213> ORGANISM: Artificial Sequence
<220> FEATURE:
<223> OTHER INFORMATION: Sequence resulting from TAV-255 deletion

<400> SEQUENCE: 2
ggtgttttgg                                                          10

<210> SEQ ID NO 3
<211> LENGTH: 9
<212> TYPE: DNA
<213> ORGANISM: Artificial Sequence
<220> FEATURE:
<223> OTHER INFORMATION: Sequence resulting from exemplary E1A promoter
      TATA box deletion

<400> SEQUENCE: 3 ctaggactg                                                           9

<210> SEQ ID NO 4
<211> LENGTH: 8
<212> TYPE: DNA
<213> ORGANISM: Adenovirus type 5

<400> SEQUENCE: 4 ctgacctc                                                            8

<210> SEQ ID NO 5
<211> LENGTH: 8
<212> TYPE: DNA
<213> ORGANISM: Adenovirus type 5

<400> SEQUENCE: 5 tcaccagg                                                            8

<210> SEQ ID NO 6
<211> LENGTH: 46
<212> TYPE: DNA
<213> ORGANISM: Artificial Sequence
<220> FEATURE:
<223> OTHER INFORMATION: Exempalry modified E1b-19k region

<400> SEQUENCE: 6
atcttggtta catctgacct cgtcgagtca ccaggcgctt ttccaa                   46

<210> SEQ ID NO 7
<211> LENGTH: 1185
<212> TYPE: DNA
<213> ORGANISM: Artificial Sequence
<220> FEATURE:
<223> OTHER INFORMATION: mTGFB-Trap

<400> SEQUENCE: 7
atgggtcggg ggctgctccg gggcctgtgg ccgctgcata tcgtcctgtg gacgcgcatc    60
gccagcacga tcccgccgca cgttcccaag tcggttaaca gtgatgtcat ggccagcgac   120
aatggcggtg cggtcaagct tccacagctg tgcaagtttt gcgatgtgag actgtccact   180
tgcgacaacc agaagtcctg catgagcaac tgcagcatca cggccatctg tgagaagccg   240
catgaagtct gctggccgt gtggaggaag aacgacaaga acattactct ggagacggtt   300
tgccacgacc ccaagctcac ctaccacggc ttcactctgg aagatgccgc ttctcccaag   360

```
tgtgtcatga aggaaaagaa aagggcgggc gagactttct tcatgtgtgc ctgtaacatg    420
gaagagtgca acgattacat catcttttcg gaagaataca ccaccagcag tcccgacagc    480
accaaggtgg acaagaaaat tgtgcccagg gattgtggtt gtaagccttg catatgtaca    540
gtcccagaag tatcatctgt cttcatcttc cccccaaagc ccaaggatgt gctcaccatt    600
actctgactc ctaaggtcac gtgtgttgtg gtagacatca gcaaggatga tcccgaggtc    660
cagttcagct ggtttgtaga tgatgtggag gtgcacacag ctcagacgca accccgggag    720
gagcagttca acagcacttt ccgctcagtc agtgaacttc ccatcatgca ccaggactgg    780
ctcaatggca aggagttcaa atgcagggtc aacagtgcag cttccctgc ccccatcgag     840 aaaaccatct ccaaaaccaa aggcagaccg aaggctccgc aggtgtacac cattccacct    900
cccaaggagc agatggccaa ggataaagtc agtctgacct gcatgataac agacttcttc    960
cctgaagaca ttactgtgga gtggcagtgg aatgggcagc cagcggagaa ctacaagaac    1020
actcagccca tcatggacac agatggctct tacttcgtct acagcaagct caatgtgcag    1080
aagagcaact gggaggcagg aaatactttc acctgctctg tgttacatga gggcctgcac    1140
aaccaccata ctgagaagag cctctcccac tctcctggta aatga                   1185
```

<210> SEQ ID NO 8  
<211> LENGTH: 8  
<212> TYPE: DNA  
<213> ORGANISM: Artificial Sequence  
<220> FEATURE:  
<223> OTHER INFORMATION: Sequence resulting from exemplary E1A promoter  
      TATA box deletion

<400> SEQUENCE: 8 agtgcccg                                                                    8

<210> SEQ ID NO 9  
<211> LENGTH: 8  
<212> TYPE: DNA  
<213> ORGANISM: Artificial Sequence  
<220> FEATURE:  
<223> OTHER INFORMATION: Sequence resulting from exemplary E1A promoter  
      TATA box deletion

<400> SEQUENCE: 9 tattcccg                                                                    8

<210> SEQ ID NO 10  
<211> LENGTH: 10  
<212> TYPE: DNA  
<213> ORGANISM: Artificial Sequence  
<220> FEATURE:  
<223> OTHER INFORMATION: Sequence resulting from exemplary E1A promoter  
      CAAT box deletion

<400> SEQUENCE: 10
ttccgtggcg                                                                 10

<210> SEQ ID NO 11  
<211> LENGTH: 8  
<212> TYPE: DNA  
<213> ORGANISM: Adenovirus type 5

<400> SEQUENCE: 11 cagtatga                                                                    8

```
<210> SEQ ID NO 12
<211> LENGTH: 10
<212> TYPE: DNA
<213> ORGANISM: Adenovirus type 5

<400> SEQUENCE: 12
taataaaaaa                                                                10

<210> SEQ ID NO 13
<211> LENGTH: 8
<212> TYPE: DNA
<213> ORGANISM: Adenovirus type 5

<400> SEQUENCE: 13 tgccttaa                                                                   8

<210> SEQ ID NO 14
<211> LENGTH: 11
<212> TYPE: DNA
<213> ORGANISM: Adenovirus type 5

<400> SEQUENCE: 14
taaaaaaaaa t                                                              11
```

METHOD FOR PRODUCING RECOMBINANT ONCOLYTIC ADENOVIRUS WITH MODIFIED E1A CANCER-SPECIFIC PROMOTER

CROSS-REFERENCE TO RELATED APPLICATIONS

This application is a § 371 National Stage of International (PCT) Patent Application No. PCT/US2018/026977, filed Apr. 10, 2018, which claims the benefit of, and priority to, U.S. Provisional Patent Application No. 62/483,837 filed Apr. 10, 2017, the entire disclosures of each of which are hereby incorporated by reference herein for all purposes.

FIELD OF THE INVENTION

The field of the invention relates to methods for producing a recombinant virus, e.g., a recombinant oncolytic adenovirus.

BACKGROUND

Despite extensive knowledge of the underlying molecular mechanisms that cause cancer, most advanced cancers remain incurable with current chemotherapy and radiation protocols. Oncolytic viruses have emerged as a platform technology that has the potential to significantly augment current standard treatment for a variety of malignancies (Kumar, S. et al. (2008) CURRENT OPINION IN MOLECULAR THERAPEUTICS 10(4):371-379; Kim, D. (2001) EXPERT OPINION ON BIOLOGICAL THERAPY 1(3):525-538; Kim D. (2000) ONCOGENE 19(56):6660-6669). These viruses have shown promise as oncolytic agents that not only directly destroy malignant cells via an infection-to-reproduction-to-lysis chain reaction but also indirectly induce anti-tumor immunity. These immune stimulatory properties have been augmented with the insertion of therapeutic transgenes that are copied and expressed each time the virus replicates.

Previously developed oncolytic viruses include the oncolytic serotype 5 adenovirus (Ad5) referred to as TAV-255 that is transcriptionally attenuated in normal cells but transcriptionally active in cancer cells (see, PCT Publication No. WO2010/101921). It is believed that the mechanism by which the TAV-255 vector achieves this tumor selectivity is through targeted deletion of three transcriptional factor (TF) binding sites for the transcription factors Pea3 and E2F, proteins that regulate adenovirus expression of E1a, the earliest gene to be transcribed after virus entry into the host cell, through binding to specific DNA sequences.

Despite the efforts to date, there is a need for improved viruses for treating cancers and hyperproliferative disorders in human patients, and improved methods for producing recombinant viruses.

SUMMARY OF THE INVENTION

The invention is based, in part, upon the discovery that an A549 host cell, e.g., a SF-BMAdR 281 A549 host cell, can be used to produce large quantities of a recombinant virus, e.g., an oncolytic adenovirus. It has surprisingly has been found that certain recombinant viruses, e.g., recombinant oncolytic adenoviruses, grow to higher densities in a replication permissive environment in serum-free and suspension-adapted A549 cells than in HEK293 cells, which are widely used for viral vector production.

Accordingly, in one aspect, the invention provides a method for producing a recombinant virus comprising: (a) infecting an A549 host cell with a recombinant virus to produce an infected A549 host cell; and (b) suspension culturing the infected A549 host cell in a serum-free medium, under conditions (e.g., in a replication permissive environment) to permit replication of the recombinant virus, thereby to produce the recombinant virus. In certain embodiments, the A549 host cell is a SF-BMAdR 281 A549 host cell. In certain embodiments, the infected A549 host cell is cultured for at least 3 days.

The method may further comprise, after step (b), the step of purifying the recombinant virus. The step of purifying the recombinant virus may comprise one or more of lysing the infected A549 host cell, nuclease treatment, and ion exchange chromatography, e.g., anion exchange chromatography. In certain embodiments, the step of purifying the recombinant virus comprises: (i) lysing the infected A549 host cell to produce a cell lysate; (ii) treating the cell lysate with nuclease to produce a treated cell lysate; and (iii) purifying the recombinant virus from the treated cell lysate by ion exchange chromatography, e.g., anion exchange chromatography.

The method may result in a greater yield of recombinant virus than a comparable method for producing a recombinant virus. For example, in certain embodiments, the method results in at least 5×, 10×, or 20× more recombinant virus compared to a similar method (e.g., an otherwise identical method) that comprises, in step (a), infecting a HEK293 host cell with a recombinant virus to produce an infected HEK293 host cell, and, in step (b), suspension culturing the infected HEK293 host cell in a serum-free medium, under conditions (e.g., in a replication permissive environment) to permit replication of the recombinant virus. In certain embodiments, the method results in at least 5×, 10×, or 20× more recombinant virus compared to a similar method (e.g., an otherwise identical method) that comprises, in step (b), adherent culturing the infected A549 host cell in a serum-free medium, under conditions (e.g., in a replication permissive environment) to permit replication of the recombinant virus. In certain embodiments, the method results in at least 5×, 10×, or 20× more recombinant virus compared to a similar method (e.g., an otherwise identical method) that comprises, in step (b), suspension culturing the infected A549 host cell in a serum-containing medium, under conditions (e.g., a replication permissive environment) to permit replication of the recombinant virus.

In certain embodiments, the recombinant virus is an adenovirus, e.g., a type 5 adenovirus, or an adeno-associated virus. In certain embodiments, the recombinant virus is a recombinant oncolytic virus. In certain embodiments, the recombinant virus is a recombinant oncolytic adenovirus.

In another aspect, the invention provides a method for producing a recombinant oncolytic adenovirus comprising: (a) infecting an A549 host cell with a recombinant oncolytic adenovirus to produce an infected A549 host cell; and (b) suspension culturing the infected A549 host cell in a serum-free medium, under conditions (e.g., in a replication permissive environment) to permit replication of the recombinant oncolytic adenovirus, thereby to produce the recombinant oncolytic adenovirus. In certain embodiments, the A549 host cell is a SF-BMAdR 281 A549 host cell. In certain embodiments, the infected A549 host cell is cultured for at least 3 days.

The method may further comprise, after step (b), the step of purifying the recombinant oncolytic adenovirus. The step of purifying the recombinant oncolytic adenovirus may comprise one or more of lysing the infected A549 host cell, nuclease treatment, and ion exchange chromatography, e.g., anion exchange chromatography. In certain embodiments, the step of purifying the recombinant oncolytic adenovirus comprises: (i) lysing the infected A549 host cell to produce a cell lysate; (ii) treating the cell lysate with nuclease to produce a treated cell lysate; and (iii) purifying the recombinant virus from the treated cell lysate by ion exchange chromatography, e.g., anion exchange chromatography.

The method may result in a greater yield of recombinant oncolytic adenovirus than a comparable method for producing a recombinant oncolytic adenovirus. For example, in certain embodiments, the method results in at least 5×, 10×, or 20× more recombinant oncolytic adenovirus compared to a similar method (e.g., an otherwise identical method) that comprises, in step (a), infecting a HEK293 host cell with a recombinant oncolytic adenovirus to produce an infected HEK293 host cell, and, in step (b), suspension culturing the infected HEK293 host cell in a serum-free medium, under conditions (e.g., in a replication permissive environment) to permit replication of the recombinant oncolytic adenovirus. In certain embodiments, the method results in at least 5×, 10×, or 20× more recombinant oncolytic adenovirus compared to a similar method (e.g., an otherwise identical method) that comprises, in step (b), adherent culturing the infected A549 host cell in a serum-free medium, under conditions (e.g., in a replication permissive environment) to permit replication of the recombinant oncolytic adenovirus. In certain embodiments, the method results in at least 5×, 10×, or 20× more recombinant oncolytic adenovirus compared to a similar method (e.g., an otherwise identical method) that comprises, in step (b), suspension culturing the infected A549 host cell in a serum-containing medium, under conditions (e.g., in a replication permissive environment) to permit replication of the recombinant oncolytic adenovirus.

In another aspect, the invention provides a method for producing a recombinant oncolytic adenovirus comprising: (a) introducing a nucleic acid comprising a nucleotide sequence encoding a recombinant oncolytic adenovirus into an A549 host cell; and (b) suspension culturing the A549 host cell in a serum-free medium, under conditions (e.g., in a replication permissive environment) to permit production of the recombinant oncolytic adenovirus, thereby to produce the recombinant oncolytic adenovirus. In certain embodiments, the A549 host cell is a SF-BMAdR 281 A549 host cell. In certain embodiments, the A549 host cell is cultured for at least 3 days.

The method may further comprise, after step (b), the step of purifying the recombinant oncolytic adenovirus. The step of purifying the recombinant oncolytic adenovirus may comprise one or more of lysing the A549 host cell, nuclease treatment, and ion exchange chromatography, e.g., anion exchange chromatography. In certain embodiments, the step of purifying the recombinant oncolytic adenovirus comprises: (i) lysing the A549 host cell to produce a cell lysate; (ii) treating the cell lysate with nuclease to produce a treated cell lysate; and (iii) purifying the recombinant virus from the treated cell lysate by ion exchange chromatography, e.g., anion exchange chromatography.

The method may result in a greater yield of recombinant oncolytic adenovirus than a comparable method for producing a recombinant oncolytic adenovirus. For example, in certain embodiments, the method results in at least 5×, 10×, or 20× more recombinant oncolytic adenovirus compared to a similar method (e.g., an otherwise identical method) that comprises, in step (a), introducing a nucleic acid comprising a nucleotide sequence encoding a recombinant oncolytic adenovirus into a HEK293 host cell, and, in step (b), suspension culturing the HEK293 host cell in a serum-free medium, under conditions (e.g., in a replication permissive environment) to permit production of the recombinant oncolytic adenovirus. In certain embodiments, the method results in at least 5×, 10×, or 20× more recombinant oncolytic adenovirus compared to a similar method (e.g., an otherwise identical method) that comprises, in step (b), adherent culturing the A549 host cell in a serum-free medium, under conditions (e.g., in a replication permissive environment) to permit replication of the recombinant oncolytic adenovirus. In certain embodiments, the method results in at least 5×, 10×, or 20× more recombinant oncolytic adenovirus compared to a similar method (e.g., an otherwise identical method) that comprises, in step (b), suspension culturing the A549 host cell in a serum-containing medium, under conditions (e.g., in a replication permissive environment) to permit replication of the recombinant oncolytic adenovirus.

In certain embodiments, the recombinant oncolytic adenovirus comprises an E1a promoter having a deletion of a functional Pea3 binding site. For example, the virus may comprise a deletion of nucleotides corresponding to about −300 to about −250 upstream of the initiation site of E1a, e.g., a deletion of nucleotides corresponding to −305 to −255 or −304 to −255 upstream of the initiation site of E1a. In certain embodiments, the deletion comprises a deletion of nucleotides corresponding to 195-244 of the Ad5 genome (SEQ ID NO: 1), and/or the E1a promoter comprises the sequence GGTGTTTTGG (SEQ ID NO: 2).

In certain embodiments, the recombinant oncolytic adenovirus comprises an E1a promoter having a deletion of a functional TATA box, e.g., the deletion of an entire TATA box. For example, in certain embodiments, the virus comprises a deletion of nucleotides corresponding to −27 to −24, −31 to −24, −44 to +54, or −146 to +54 of the adenovirus type 5 E1a promoter, which correspond, respectively, to nucleotides 472 to 475, 468 to 475, 455 to 552, and 353 to 552 of the Ad5 genome (SEQ ID NO: 1). In certain embodiments, the virus comprises a polynucleotide deletion that results in a virus comprising the sequence CTAGGACTG (SEQ ID NO: 3), AGTGCCCG (SEQ ID NO: 8), or TATTCCCG (SEQ ID NO: 9), which result from joining the two polynucleotide sequences that would otherwise flank the deleted polynucleotide sequence.

In certain embodiments, the recombinant oncolytic adenovirus comprises a deletion of nucleotides corresponding to −29 to −26, −33 to −26, −44 to +52, or −148 to +52 of the adenovirus type 5 E1a promoter. In certain embodiments, the virus comprises a deletion of nucleotides corresponding to 353 to 552 of the Ad5 genome (SEQ ID NO: 1). In certain embodiments, the virus comprises a polynucleotide deletion that results in a virus comprising the sequence CTAGGACTG (SEQ ID NO: 3), which results from joining the two polynucleotide sequences that would otherwise flank the deleted polynucleotide sequence.

In certain embodiments, the recombinant oncolytic adenovirus comprises an E1a promoter having a deletion of a functional CAAT box, e.g., the deletion of an entire CAAT box. For example, in certain embodiments, the virus comprises a deletion of nucleotides corresponding to −76 to −68 of the adenovirus type 5 E1a promoter, which corresponds to nucleotides 423 to 431 of the Ad5 genome (SEQ ID NO: 1). In certain embodiments, the virus comprises a polynucleotide deletion that results in a virus comprising the sequence TTCCGTGGCG (SEQ ID NO: 10), which results from joining the two polynucleotide sequences that would otherwise flank the deleted polynucleotide sequence.

In certain embodiments, the recombinant oncolytic adenovirus comprises a nucleotide sequence encoding a transgene, which may, e.g., be inserted into an E1b-19K insertion site, wherein the E1b-19K insertion site is located between the start site of E1b-19K and the start site of E1b-55K. In certain embodiments, the E1b-19K insertion site is located between the start site of E1b-19K and the stop site of E1b-19K. In certain embodiments, the E1b-19K insertion site comprises a deletion of from about 100 to about 305, about 100 to about 300, about 100 to about 250, about 100 to about 200, about 100 to about 150, about 150 to about 305, about 150 to about 300, about 150 to about 250, or about 150 to about 200 nucleotides adjacent the start site of E1b-19K. In certain embodiments, the E1b-19K insertion site comprises a deletion of about 200 nucleotides, e.g., 202 or 203 nucleotides adjacent the start site of E1b-19K. In certain embodiments, the E1b-19K insertion site comprises a deletion corresponding to nucleotides 1714-1917 or 1714-1916 of the Ad5 genome (SEQ ID NO: 1). In certain embodiments, the nucleotide sequence encoding the transgene is inserted between nucleotides corresponding to 1714 and 1917 or between nucleotides corresponding to 1714 and 1916 of the Ad5 genome (SEQ ID NO: 1). In certain embodiments, the nucleotide sequence encoding the transgene is inserted between CTGACCTC (SEQ ID NO: 4) and TCACCAGG (SEQ ID NO: 5), e.g., the virus comprises, in a 5' to 3' orientation, CTGACCTC (SEQ ID NO: 4), the nucleotide sequence encoding the transgene, and TCACCAGG (SEQ ID NO: 5).

In certain embodiments, the nucleotide sequence encoding the transgene is not operably linked to an exogenous promoter sequence.

In certain embodiments, the transgene encodes a polypeptide selected from CD80, CD137L, IL-23, IL-23A/p19, p40, IL-27, IL-27A/p28, IL-27B/EBI3, ICAM-1, a TGF-β trap, TGF-β, CD19, CD20, IL-1, IL-3, IL-4, IL-5, IL-6, IL-8, IL-9, CD154, CD86, BORIS/CTCFL, FGF, IL-24, MAGE, NY-ESO-1, acetylcholine, interferon-gamma, DKK1/Wnt, p53, thymidine kinase, an anti-PD-1 antibody heavy chain or light chain, and an anti-PD-L1 antibody heavy chain or light chain.

In certain embodiments, the recombinant virus, e.g., the recombinant oncolytic adenovirus, may selectively replicate in a hyperproliferative cell and/or selectively express the transgene in a hyperproliferative cell. The hyperproliferative cell may be a cancer cell.

In another aspect, the invention provides a recombinant virus, e.g., a recombinant oncolytic adenovirus, produced by a method disclosed herein.

In another aspect, the invention provides a method of treating cancer in a subject in need thereof, the method comprising administering to the subject an effective amount of a recombinant virus, e.g., a recombinant oncolytic adenovirus, produced by a method disclosed herein to treat the cancer in the subject.

These and other aspects and advantages of the invention are illustrated by the following figures, detailed description and claims.

DESCRIPTION OF THE DRAWINGS

The invention can be more completely understood with reference to the following drawings.

DETAILED DESCRIPTION

Figure 1:
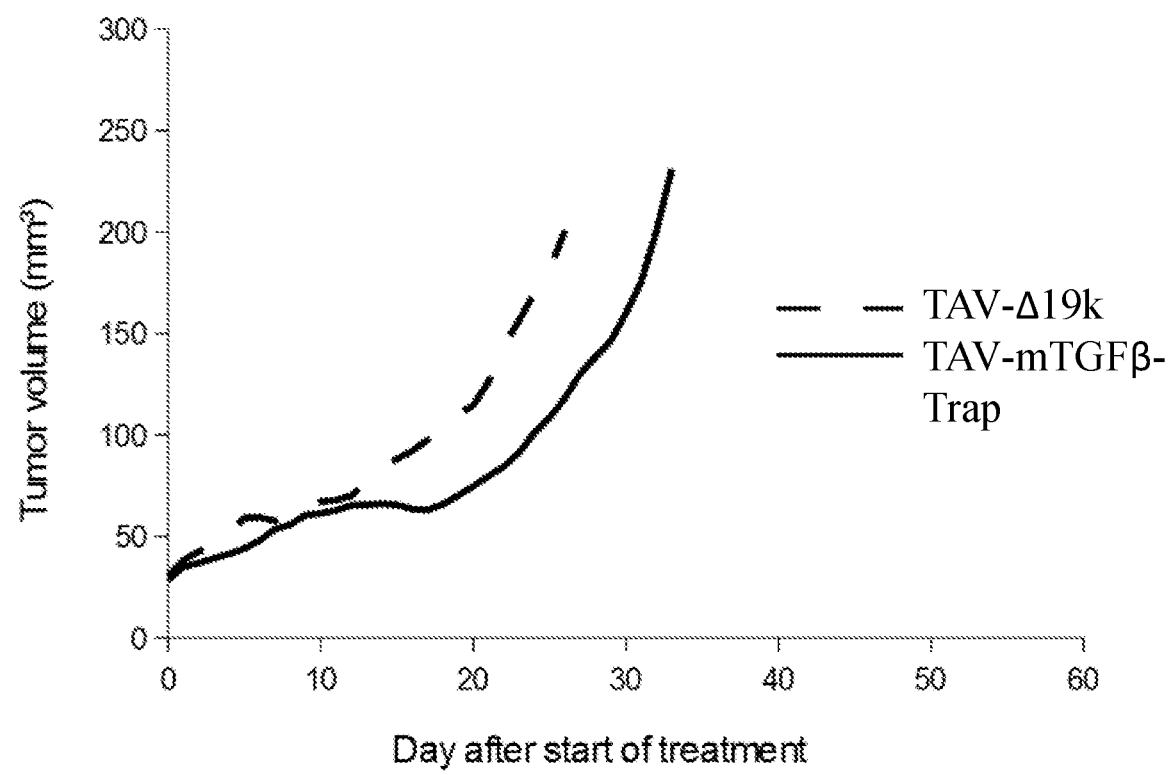
FIG. 1 is a line graph depicting mean tumor volumes in mice following treatment with the indicated virus.

The invention is based, in part, upon the discovery that an A549 host cell, e.g., a SF-BMAdR 281 A549 host cell, can be used to produce large quantities of a recombinant virus, e.g., an oncolytic adenovirus. It has surprisingly has been found that certain recombinant viruses, e.g., recombinant oncolytic adenoviruses, grow to higher densities in a replication permissive environment in serum-free and suspension-adapted A549 cells than in HEK293 cells, which are widely used for viral vector production.

Accordingly, in one aspect, the invention provides a method for producing a recombinant virus comprising: (a) infecting an A549 host cell with a recombinant virus to produce an infected A549 host cell; and (b) suspension culturing the infected A549 host cell in a serum-free medium, under conditions (e.g., in a replication permissive environment) to permit replication of the recombinant virus, thereby to produce the recombinant virus. In certain embodiments, the recombinant virus is an adenovirus, e.g., a type 5 adenovirus, or an adeno-associated virus. In certain embodiments, the recombinant virus is a recombinant oncolytic virus. In certain embodiments, the recombinant virus is a recombinant oncolytic adenovirus.

In another aspect, the invention provides a method for producing a recombinant oncolytic adenovirus comprising: (a) infecting an A549 host cell with a recombinant oncolytic adenovirus to produce an infected A549 host cell, and (b) suspension culturing the infected A549 host cell in a serum-free medium, under conditions (e.g., in a replication permissive environment) to permit replication of the recombinant oncolytic adenovirus, thereby to produce the recombinant oncolytic adenovirus.

In another aspect, the invention provides a method for producing a recombinant oncolytic adenovirus comprising: (a) introducing a nucleic acid comprising a nucleotide sequence encoding a recombinant oncolytic adenovirus into an A549 host cell, and (b) suspension culturing the A549 host cell in a serum-free medium, under conditions (e.g., in a replication permissive environment) to permit production of the recombinant oncolytic adenovirus, thereby to produce the recombinant oncolytic adenovirus. The nucleic acid can be introduced into the cell using any method known in the art, e.g., liposome-based transfection, chemical-based transfection (e.g., utilizing calcium phosphate, cationic polymers, DEAE-5 dextran, or activated dendrimers), microinjection, electroporation, nanoparticles, or cell squeezing. The nucleic acid may, for example, be part of a plasmid, or may, for example, be part of more than one plasmid.

In certain embodiments of any of the foregoing methods, the A549 host cell is a SF-BMAdR 281 A549 host cell.

An A549 host cell, e.g., an infected A549 host cell, may be cultured for at least 1 day, at least 2 days, at least 3 days, at least 4 days, at least 5 days, at least 6 days, or at least 7 days.

Following production, viral particles are recovered from the culture and optionally purified. Typical purification steps may include centrifugation, e.g., cesium chloride gradient centrifugation, clarification, enzymatic treatment, e.g., nuclease or protease treatment, chromatographic steps, e.g., ion exchange chromatography, (e.g., anion exchange chromatography), or filtration steps. Accordingly, in certain embodiments, any of the foregoing methods further comprise, after step (b), the step of purifying a recombinant virus, e.g., a recombinant oncolytic adenovirus. The step of purifying the recombinant virus, e.g., the recombinant oncolytic adenovirus, may comprise lysing an A549 host cell, e.g., an infected A549 host cell, nuclease treatment, and/or ion exchange chromatography, e.g., anion exchange chromatography. In certain embodiments, the step of purifying the recombinant virus, e.g., the recombinant oncolytic adenovirus, comprises: (i) lysing an A549 host cell, e.g., an infected A549 host cell, to produce a cell lysate; (ii) treating the cell lysate with nuclease to produce a treated cell lysate; and (iii) purifying the recombinant virus from the treated cell lysate by ion exchange chromatography, e.g., anion exchange chromatography.

In certain embodiments, any of the foregoing methods may result in a greater yield of recombinant virus, e.g., recombinant oncolytic adenovirus, than a comparable method for producing a recombinant virus. For example, in certain embodiments, a method may result in greater yield of recombinant virus, e.g., recombinant oncolytic adenovirus, compared to a similar method that is the same method but for the use of a different host cell type. Viral yield can be assayed by any method known in the art, including, e.g., qPCR, immunocytochemistry, or a luciferase reporter assay.

For example, in certain embodiments, a method results in at least 2×, at least 3×, at least 4×, at least 5×, at least 10×, at least 15×, at least 20×, at least 25×, or at least 30× more recombinant virus, e.g., recombinant oncolytic adenovirus, compared to a similar method (e.g., an otherwise identical method) that comprises, in step (a), infecting a HEK293 host cell with a recombinant virus to produce an infected HEK293 host cell, and, in step (b), suspension culturing the infected HEK293 host cell in a serum-free medium, under conditions (e.g., in a replication permissive environment) to permit replication of the recombinant virus. In certain embodiments, a method results in at least 2×, at least 3×, at least 4×, at least 5×, at least 10×, at least 15×, at least 20×, at least 25×, or at least 30× more recombinant virus, e.g., recombinant oncolytic adenovirus, compared to a similar method (e.g., an otherwise identical method) that comprises, in step (a), introducing a nucleic acid comprising a nucleotide sequence encoding a recombinant oncolytic adenovirus into a HEK293 host cell, and, in step (b), suspension culturing the HEK293 host cell in a serum-free medium, under conditions (e.g., in a replication permissive environment) to permit replication of the recombinant virus.

In certain embodiments, the method may result in greater yield of recombinant virus, e.g., recombinant oncolytic adenovirus, compared to a similar method that is the same method but for the use of adherent culture in place of suspension culture. For example, in certain embodiments, the method results in at least 2×, at least 3×, at least 4×, at least 5×, at least 10×, at least 15×, at least 20×, at least 25×, or at least 30× more recombinant virus, e.g., recombinant oncolytic adenovirus, compared to a similar method (e.g., an otherwise identical method) that comprises, in step (b), adherent culturing an A549 host cell, e.g., an infected A549 host cell, in a serum-free medium, under conditions (e.g., in a replication permissive environment) to permit replication of the recombinant virus. In certain embodiments, the method may result in greater yield of recombinant virus, e.g., recombinant oncolytic adenovirus, compared to a similar method that is the same method but for the use of serum-containing media in place of serum-free media. For example, in certain embodiments, the method results in at least 2×, at least 3×, at least 4×, at least 5×, at least 10×, at least 15×, at least 20×, at least 25×, or at least 30× more recombinant virus e.g., recombinant oncolytic adenovirus, compared to a similar method (e.g., an otherwise identical method) that comprises, in step (b), suspension culturing an A549 host cell, e.g., an infected A549 host cell, in a serum-containing medium, under conditions (e.g., in a replication permissive environment) to permit replication of the recombinant virus.

In certain embodiments, a method further comprises contacting an A549 host cell with an epigenetic agent, e.g., a DNMT, HDAC, and/or tyrosine kinase inhibitor, Exemplary epigenetic agents include vorinostat, romidepsin, azacitidine, decitabine, RRx-001 and CUDC-101. In certain embodiments, a method further comprises contacting an A549 host cell with an interferon. In certain embodiments, a method further comprises contacting an A549 host cell with an antioxidant, e.g., vitamin C, vitamin E, glutathione, or N-acetylcysteine.

Various features and aspects of the invention are discussed in more detail below.

I. Viruses

The term "virus" is used herein to refer any of the obligate intracellular parasites having no protein-synthesizing or energy-generating mechanism. The viral genome may be RNA or DNA. A recombinantly modified virus is referred to herein as a "recombinant virus." A recombinant virus may, e.g., be modified by recombinant DNA techniques to be replication deficient, conditionally replicating, or replication competent, and/or be modified by recombinant DNA techniques to include expression of exogenous transgenes. Chimeric viral vectors which exploit advantageous elements of each of the parent vector properties (See, e.g., Feng et al. (1997) NATURE BIOTECHNOLOGY 15:866-870) may also be useful in the practice of the present invention. Although it is generally favored to employ a virus from the species to be treated, in some instances it may be advantageous to use vectors derived from different species that possess favorable pathogenic features.

In certain embodiments, the recombinant virus is an oncolytic virus, e.g., a virus that exhibits tumor-selective replication and/or viral mediated lysis. In certain embodiments, the oncolytic virus allows for selective expression of a gene, e.g., a transgene. For example, in certain embodiments, the virus permits expression of the gene in neoplastic cells, but attenuates expression in normal cells. In certain embodiments, the expression of the gene in a non-hyperproliferative cell is about 90%, about 80%, about 70%, about 60%, about 50%, about 40%, about 30%, about 20%, about 10%, or about 5% of the expression of in a hyperproliferative cell. In certain embodiments, the virus exhibits no detectable expression of the gene in a non-hyperproliferative cell. Gene expression may be determined by any appropriate method known in the art, e.g., Western blot or ELISA. The hyperproliferative cell may be a cancer cell, e.g., a carcinoma, sarcoma, leukemia, lymphoma, prostate cancer, lung cancer, gastrointestinal tract cancer, colorectal cancer, pancreatic cancer, breast cancer, ovarian cancer, cervical cancer, stomach cancer, thyroid cancer, mesothelioma, liver cancer, kidney cancer, skin cancer, head and neck cancer, or brain cancer cell.

In certain embodiments, the recombinant virus is an adenovirus or an adeno-associated virus. In certain embodiments, the recombinant virus is an adenovirus. Adenoviruses are medium-sized (90-100 nm), non-enveloped (naked), icosahedral viruses composed of a nucleocapsid and a double-stranded linear DNA genome. Adenoviruses replicate in the nucleus of mammalian cells using the host's replication machinery. The term "adenovirus" refers to any virus in the genus Adenoviridiae including, but not limited to, human, bovine, ovine, equine, canine, porcine, murine, and simian adenovirus subgenera. In particular, human adenoviruses includes the A-F subgenera as well as the individual serotypes thereof, the individual serotypes and A-F subgenera including but not limited to human adenovirus types 1, 2, 3, 4, 4a, 5, 6, 7, 8, 9, 10, 11 (Ad11a and Ad11p), 12, 13, 14, 15, 16, 17, 18, 19, 19a, 20, 21, 22, 23, 24, 25, 26, 27, 28, 29, 30, 31, 32, 33, 34, 34a, 35, 35p, 36, 37, 38, 39, 40, 41, 42, 43, 44, 45, 46, 47, 48, and 91. Preferred are recombinant viruses derived from human adenovirus types 2 and 5. Unless stated otherwise, all adenovirus type 5 nucleotide numbers are relative to the NCBI reference sequence AC_000008.1, which is depicted herein in SEQ ID NO: 1.

The adenovirus replication cycle has two phases: an early phase, during which 4 transcription units E1, E2, E3, and E4 are expressed, and a late phase which occurs after the onset of viral DNA synthesis when late transcripts are expressed primarily from the major late promoter (MLP). The late messages encode most of the virus's structural proteins. The gene products of E1, E2 and E4 are responsible for transcriptional activation, cell transformation, viral DNA replication, as well as other viral functions, and are necessary for viral growth.

The term "operably linked" refers to a linkage of polynucleotide elements in a functional relationship. A nucleic acid sequence is "operably linked" when it is placed into a functional relationship with another nucleic acid sequence. For instance, a promoter or enhancer is operably linked to a gene if it affects the transcription of the gene. Operably linked nucleotide sequences are typically contiguous. However, as enhancers generally function when separated from the promoter by several kilobases and intronic sequences may be of variable lengths, some polynucleotide elements may be operably linked but not directly flanked and may even function in trans from a different allele or chromosome.

In certain embodiments, the recombinant virus has one or more modifications to a regulatory sequence or promoter. A modification to a regulatory sequence or promoter comprises a deletion, substitution, or addition of one or more nucleotides compared to the wild-type sequence of the regulatory sequence or promoter.

In certain embodiments, the modification of a regulatory sequence or promoter comprises a modification of sequence of a transcription factor binding site to reduce affinity for the transcription factor, for example, by deleting a portion thereof, or by inserting a single point mutation into the binding site. In certain embodiments, the additional modified regulatory sequence enhances expression in neoplastic cells, but attenuates expression in normal cells.

In certain embodiments, the modified regulatory sequence is operably linked to a sequence encoding a protein. In certain embodiments, at least one of the adenoviral E1a and E1b genes (coding regions) is operably linked to a modified regulatory sequence. In certain embodiments, the E1a gene is operably linked to the modified regulatory sequence.

The E1a regulatory sequence contains five binding sites for the transcription factor Pea3, designated Pea3 I, Pea3 II, Pea3 III, Pea3 IV, and Pea3 V, where Pea3 I is the Pea3 binding site most proximal to the E1a start site, and Pea3 V is most distal. The E1a regulatory sequence also contains binding sites for the transcription factor E2F, hereby designated E2F I and E2F II, where E2F I is the E2F binding site most proximal to the E1a start site, and E2F II is more distal. From the E1a start site, the binding sites are arranged: Pea3 I, E2F I, Pea3 II, E2F II, Pea3 III, Pea3 IV, and Pea3 V.

In certain embodiments, at least one of these seven binding sites, or a functional binding site, is deleted. As used herein, a "functional binding site" refers to a binding site that is capable of binding to a respective binding partner, e.g., a transcription factor, e.g., a binding site that has at least 100%, at least 90%, at least 80%, at least 70%, at least 60%, at least 50%, or at least 40%, of the binding activity of a corresponding wild-type binding site sequence. As used herein, a "non-functional binding site" refers to a binding site that, e.g., has less than 30%, less than 20%, less than 10%, or 0% of the binding activity of a corresponding wild-type binding site sequence.

In certain embodiments, a recombinant adenovirus, e.g., a recombinant oncolytic adenovirus, comprises an E1a promoter having a deletion of a functional Pea3 binding site, e.g., the deletion of an entire Pea3 binding site. As used herein, a "functional Pea3 binding site" refers to a Pea3 binding site that is capable of binding to its respective transcription factor (e.g., Pea3), e.g., a Pea3 binding site that has at least 100%, at least 90%, at least 80%, at least 70%, at least 60%, at least 50%, or at least 40%, of the Pea3 binding activity of a corresponding wild-type Pea3 binding site sequence. As used herein, a "non-functional Pea3 binding site" refers to a Pea3 binding site that, e.g., has less than 30%, less than 20%, less than 10%, or 0% of the Pea3 binding activity of a corresponding wild-type Pea3 binding site sequence. Assays for determining whether a Pea3 binding site binds to Pea3 are known in the art. Exemplary binding assays include electrophoretic mobility shift assays, chromatin immunoprecipitation assays, and DNAse footprinting assays.

In certain embodiments, at least one Pea3 binding site, or a functional Pea3 binding site, is deleted. The deleted Pea3 binding site can be Pea3 I, Pea3 II, Pea3 III, Pea3 IV, and/or Pea3 V. In certain embodiments, the deleted Pea3 binding site is Pea3 II, Pea3 III, Pea3 IV, and/or Pea3 V. In certain embodiments, the deleted Pea3 binding site is Pea3 IV and/or Pea3 V. In certain embodiments, the deleted Pea3 binding site is Pea3 II and/or Pea3 III. In certain embodiments, the deleted Pea3 binding site is both Pea3 II and Pea3 III. In certain embodiments, the Pea3 I binding site, or a functional Pea3 I binding site, is retained.

In certain embodiments, at least one E2F binding site, or a functional E2F binding site, is deleted. In certain embodiments, at least one E2F binding site, or a functional E2F binding site, is retained. In certain embodiments, the retained E2F binding site is E2F I and/or E2F II. In certain embodiments, the retained E2F binding site is E2F II. In certain embodiments, the recombinant adenovirus, e.g., recombinant oncolytic adenovirus, may comprise a deletion of at least one E2F binding site, or a functional portion thereof, and not comprise a deletion of a Pea3 binding site. In certain embodiments, the total deletion consists essentially of one or more of Pea3 II, Pea3 III, Pea3 IV, and/or Pea3 V. In certain embodiments, the virus has a deletion of a 50 base pair region located from −304 to −255 upstream of the E1a initiation site, e.g., corresponding to 195-244 of the Ad5 genome (SEQ ID NO: 1), hereafter referred to as the TAV-255 deletion. In certain embodiments, the TAV-255 deletion results in an E1a promoter that comprises the sequence GGTGTTTTGG (SEQ ID NO: 2).

In certain embodiments, a recombinant adenovirus, e.g., a recombinant oncolytic adenovirus, comprises an E1a promoter having a deletion of a functional TATA box, e.g., the deletion of an entire TATA box. As used herein, a "functional TATA box" refers to a TATA box that is capable of binding to a TATA box binding protein (TBP), e.g., a TATA box that has at least 100%, at least 90%, at least 80%, at least 70%, at least 60%, at least 50%, or at least 40%, of the TBP binding activity of a corresponding wild-type TATA box sequence. As used herein, a "non-functional TATA box" refers to a TATA box that, e.g., has less than 30%, less than 20%, less than 10%, or 0% of the TBP binding activity of a corresponding wild-type TATA box sequence. Assays for determining whether a TBP binds to a TATA box are known in the art. Exemplary binding assays include electrophoretic mobility shift assays, chromatin immunoprecipitation assays, and DNAse footprinting assays.

For example, in certain embodiments, a recombinant adenovirus, e.g., a recombinant oncolytic adenovirus, comprises a deletion of nucleotides corresponding to −27 to −24, −31 to −24, −44 to +54, or −146 to +54 of the adenovirus type 5 E1a promoter, which correspond, respectively, to nucleotides 472 to 475, 468 to 475, 455 to 552, and 353 to 552 of the Ad5 genome (SEQ ID NO: 1). In certain embodiments, the virus comprises a deletion of nucleotides corresponding to −29 to −26, −33 to −26, −44 to +52, or −148 to +52 of the adenovirus type 5 E1a promoter. In certain embodiments, the virus comprises a deletion of nucleotides corresponding to 353 to 552 of the Ad5 genome (SEQ ID NO: 1). In certain embodiments, the virus comprises a polynucleotide deletion that results in a virus comprising the sequence CTAGGACTG (SEQ ID NO: 3), AGTGCCCG (SEQ ID NO: 8), or TATTCCCG (SEQ ID NO: 9), which result from joining the two polynucleotide sequences that would otherwise flank the deleted polynucleotide sequence. In certain embodiments, the virus comprises a polynucleotide deletion that results in a virus comprising the sequence CTAGGACTG (SEQ ID NO: 3), In certain embodiments, a recombinant adenovirus, e.g., a recombinant oncolytic adenovirus, comprises an E1a promoter having a deletion of a functional CAAT box, e.g., the deletion of an entire CAAT box. As used herein, a "functional CAAT box" refers to a CAAT box that is capable of binding to a C/EBP or NF-Y protein, e.g., a CAAT box that has at least 100%, at least 90%, at least 80%, at least 70%, at least 60%, at least 50%, or at least 40%, of the a C/EBP or NF-Y binding activity of a corresponding wild-type CAAT box sequence. As used herein, a "non-functional CAAT box" refers to a CAAT box that, e.g., has less than 30%, less than 20%, less than 10%, or 0% of the a C/EBP or NF-Y binding activity of a corresponding wild-type CAAT box sequence. Assays for determining whether a C/EBP or NF-Y protein binds to a CAAT box are known in the art. Exemplary binding assays include electrophoretic mobility shift assays, chromatin immunoprecipitation assays, and DNAse footprinting assays.

For example, in certain embodiments, a recombinant adenovirus, e.g., a recombinant oncolytic adenovirus, comprises a deletion of nucleotides corresponding to −76 to −68 of the adenovirus type 5 E1a promoter, which correspond to nucleotides 423 to 431 of the Ad5 genome (SEQ ID NO: 1). In certain embodiments, the virus comprises a polynucleotide deletion that results in a virus comprising the sequence TTCCGTGGCG (SEQ ID NO: 10), which results from joining the two polynucleotide sequences that would otherwise flank the deleted polynucleotide sequence.

The adenoviral E1b-19k gene functions primarily as an anti-apoptotic gene and is a homolog of the cellular anti-apoptotic gene, BCL-2. Since host cell death prior to maturation of the progeny viral particles would restrict viral replication, E1b-19k is expressed as part of the E1 cassette to prevent premature cell death thereby allowing the infection to proceed and yield mature virions. Accordingly, in certain embodiments, a recombinant adenovirus, e.g., a recombinant oncolytic adenovirus, is provided that includes an E1b-19K insertion site, e.g., the recombinant adenovirus has a nucleotide sequence encoding a transgene inserted into an E1b-19K insertion site. In certain embodiments, the insertion site is located between the start site of E1b-19K (i.e., the nucleotide sequence encoding the start codon of E1b-19k, e.g., corresponding to nucleotides 1714-1716 of SEQ ID NO: 1) and the start site of E1b-55K (i.e., the nucleotide sequence encoding the start codon of E1b-55k, e.g., corresponding to nucleotides 2019-2021 of SEQ ID NO: 1). In certain embodiments, the E1b-19K insertion site is located between the start site of E1b-19K (i.e., the nucleotide sequence encoding the start codon of E1b-19k, e.g., corresponding to nucleotides 1714-1716 of SEQ ID NO: 1) and the stop site of E1b-19K (i.e., the nucleotide sequence encoding the stop codon of E1b-19k, e.g., corresponding to nucleotides 2242-2244 of SEQ ID NO: 1).

Throughout the description and claims, an insertion between two sites, for example, an insertion between (i) a start site of a first gene (e.g., E1b-19k) and a start site of a second gene, (e.g., E1b-55K), (ii) a start site of a first gene and a stop site of a second gene, (iii) a stop site of a first gene and start site of a second gene, or (iv) a stop site of first gene and a stop site of a second gene, is understood to mean that all or a portion of the nucleotides constituting a given start site or a stop site surrounding the insertion may be present or absent in the final virus. Similarly, an insertion between two nucleotides is understood to mean that the nucleotides surrounding the insertion may be present or absent in the final virus.

In certain embodiments, the E1b-19K insertion site comprises a deletion of from about 100 to about 305, about 100 to about 300, about 100 to about 250, about 100 to about 200, about 100 to about 150, about 150 to about 305, about 150 to about 300, about 150 to about 250, or about 150 to about 200 nucleotides adjacent the start site of E1b-19K. In certain embodiments, the E1b-19K insertion site comprises a deletion of about 200 nucleotides, e.g., 202 or 203 nucleotides adjacent the start site of E1b-19K. In certain embodiments, the E1b-19K insertion site comprises a deletion corresponding to nucleotides 1714-1917 or 1714-1916 of the Ad5 genome (SEQ ID NO: 1). In certain embodiments, a nucleotide sequence encoding a transgene is inserted between nucleotides corresponding to 1714 and 1917 or between nucleotides corresponding to 1714 and 1916 of the Ad5 genome (SEQ ID NO: 1). In certain embodiments, a nucleotide sequence encoding a transgene is inserted between CTGACCTC (SEQ ID NO: 4) and TCACCAGG (SEQ ID NO: 5), e.g., the recombinant adenovirus comprises, in a 5' to 3' orientation, CTGACCTC (SEQ ID NO: 4), a nucleotide sequence encoding a transgene, and TCACCAGG (SEQ ID NO: 5). CTGACCTC (SEQ ID NO: 4) and TCACCAGG (SEQ ID NO: 5) define unique boundary sequences for the E1b-19K insertion site within the Ad5 genome (SEQ ID NO: 1). Throughout the description and claims, a deletion adjacent a site, for example, a deletion adjacent a start site of a gene or a deletion adjacent a stop site of a gene, is understood to mean that the deletion may include a deletion of all, a portion, or none of the nucleotides constituting a given start site or a stop site.

In certain embodiments, a recombinant adenovirus, e.g., a recombinant oncolytic adenovirus, is provided that includes an E3 insertion site, e.g., the recombinant adenovirus has a nucleotide sequence encoding a transgene inserted into an E3 insertion site. In certain embodiments, the insertion site is located between the stop site of pVIII (i.e., the nucleotide sequence encoding the stop codon of pVIII, e.g., corresponding to nucleotides 27855-27857 of SEQ ID NO: 1) and the start site of Fiber (i.e., the nucleotide sequence encoding the start codon of Fiber, e.g., corresponding to nucleotides 31042-31044 of SEQ ID NO: 1). In certain embodiments, the E3 insertion site comprises a deletion of from about 500 to about 3185, from about 500 to about 3000, from about 500 to about 2500, from about 500 to about 2000, from about 500 to about 1500, from about 500 to about 1000, from about 1000 to about 3185, from about 1000 to about 3000, from about 1000 to about 2500, from about 1000 to about 2000, from about 1000 to about 1500, from about 1500 to about 3185, from about 1500 to about 3000, from about 1500 to about 2000, from about 2000 to about 3185, from about 2000 to about 3000, from about 2000 to about 2500, from about 2500 to about 3185, from about 2500 to about 3000, or from about 3000 to about 3185 nucleotides. In certain embodiments, the E3 insertion site is located between the stop site of E3-10.5K (i.e., the nucleotide sequence encoding the stop codon of E3-10.5K, e.g., corresponding to nucleotides 29770-29772 of SEQ ID NO: 1) and the stop site of E3-14.7K (i.e., the nucleotide sequence encoding the stop codon of E3-14.7K, e.g., corresponding to nucleotides 30837-30839 of SEQ ID NO: 1). In certain embodiments, the E3 insertion site comprises a deletion of from about 500 to about 1551, from about 500 to about 1500, from about 500 to about 1000, from about 1000 to about 1551, from about 1000 to about 1500, or from about 1500 to about 1551 nucleotides adjacent the stop site of E3-10.5K. In certain embodiments, the E3 insertion site comprises a deletion of about 1050 nucleotides adjacent the stop site of E3-10.5K, e.g., the E3 insertion site comprises a deletion of 1063 or 1064 nucleotides adjacent the stop site of E3-10.5K. In certain embodiments, the E3 insertion site comprises a deletion corresponding to the Ad5 dl309 E3 deletion. In certain embodiments, the E3 insertion site comprises a deletion corresponding to nucleotides 29773-30836 of the Ad5 genome (SEQ ID NO: 1), or, a nucleotide sequence encoding a transgene is inserted between nucleotides corresponding to 29773 and 30836 of the Ad5 genome (SEQ ID NO: 1). In certain embodiments, a nucleotide sequence encoding a transgene is inserted between CAGTATGA (SEQ ID NO: 11) and TAATAAAAAA (SEQ ID NO: 12), e.g., the recombinant adenovirus comprises, in a 5' to 3' orientation, CAGTATGA (SEQ ID NO: 11), a nucleotide sequence encoding a transgene, and TAATAAAAAA (SEQ ID NO: 12). CAGTATGA (SEQ ID NO: 11) and TAATAAAAAA (SEQ ID NO: 12) define unique boundary sequences for an E3 insertion site within the Ad5 genome (SEQ ID NO: 1).

In certain embodiments, the E3 insertion site is located between stop site of E3-gp19K (i.e., the nucleotide sequence encoding the stop codon of E3-gp19K, e.g., corresponding to nucleotides 29215-29217 of SEQ ID NO: 1) and the stop site of E3-14.7K (i.e., the nucleotide sequence encoding the stop codon of E3-14.7K, e.g., corresponding to nucleotides 30837-30839 of SEQ ID NO: 1). In certain embodiments, the E3 insertion site comprises a deletion of from about 500 to about 1824, from about 500 to about 1500, from about 500 to about 1000, from about 1000 to about 1824, from about 1000 to about 1500, or from about 1500 to about 1824 nucleotides adjacent the stop site of E3-gp19K. In certain embodiments, the E3 insertion site comprises a deletion of about 1600 nucleotides adjacent the stop site of E3-gp19K. e.g., the E3 insertion site comprises a deletion of 1622 nucleotides adjacent the stop site of E3-gp19K. In certain embodiments, the E3 insertion site comprises a deletion corresponding to nucleotides 29218-30839 of the Ad5 genome (SEQ ID NO: 1). In certain embodiments, a nucleotide sequence encoding a transgene is inserted between nucleotides corresponding to 29218 and 30839 of the Ad5 genome (SEQ ID NO: 1). In certain embodiments, a nucleotide sequence encoding a transgene is inserted between TGCCTTAA (SEQ ID NO: 13) and TAAAAAAAAAT (SEQ ID NO: 14), e.g., the recombinant adenovirus comprises, in a 5' to 3' orientation, TGCCTTAA (SEQ ID NO: 13), a nucleotide sequence encoding a transgene, and TAAAAAAAAAT (SEQ ID NO: 14). TGCCTTAA (SEQ ID NO: 13) and TAAAAAAAAAT (SEQ ID NO: 14) define unique boundary sequences for an E3 insertion site within the Ad5 genome (SEQ ID NO: 1).

In certain embodiments, a recombinant adenovirus, e.g., a recombinant oncolytic adenovirus, comprises an E4 deletion. In certain embodiments, the E4 deletion is located between the start site of E4-ORF6/7 (i.e., the nucleotide sequence encoding the start codon of E4-ORF6/7, e.g., corresponding to nucleotides 34075-34077 of SEQ ID NO: 1) and the right inverted terminal repeat (ITR; e.g., corresponding to nucleotides 35836-35938 of SEQ ID NO: 1). In certain embodiments, the E4 deletion is located between the start site of E4-ORF6/7 and the start site of E4-ORF1 (i.e., the nucleotide sequence encoding the start codon of E4-ORF1, e.g., corresponding to nucleotides 35524-35526 of SEQ ID NO: 1). In certain embodiments, the E4 deletion comprises a deletion of a nucleotide sequence between the start site of E4-ORF6/7 and the start site of E4-ORF1. In certain embodiments, the E4 deletion comprises a deletion of from about 500 to about 2500, from about 500 to about 2000, from about 500 to about 1500, from about 500 to about 1000, from about 1000 to about 2500, from about 1000 to about 2000, from about 1000 to about 1500, from about 1500 to about 2500, from about 1500 to about 2000, or from about 2000 to about 2500 nucleotides. In certain embodiments, the E4 deletion comprises a deletion of from about 250 to about 1500, from about 250 to about 1250, from about 250 to about 1000, from about 250 to about 750, from about 250 to about 500, from 500 to about 1500, from about 500 to about 1250, from about 500 to about 1000, from about 500 to about 750, from 750 to about 1500, from about 750 to about 1250, from about 750 to about 1000, from about 1000 to about 1500, or from about 1000 to about 1250 nucleotides adjacent the start site of E4-ORF6/7. In certain embodiments, the E4 deletion comprises a deletion of about 1450 nucleotides adjacent the start site of E4-ORF6/7, e.g., the E4 deletion comprises a deletion of about 1449 nucleotides adjacent the start site of E4-ORF6/7. In certain embodiments, the E4 deletion comprises a deletion corresponding to nucleotides 34078-35526 of the Ad5 genome (SEQ ID NO: 1).

Nucleic acids encoding viral genes can be incorporated into plasmids and introduced into host cells through conventional transfection or transformation techniques. Specific production and purification conditions will vary depending upon the virus and the production system employed. For adenovirus, the traditional method for the generation of viral particles is co-transfection followed by subsequent in vivo recombination of a shuttle plasmid (usually containing a small subset of the adenoviral genome and optionally containing a potential transgene an expression cassette) and an adenoviral helper plasmid (containing most of the entire adenoviral genome). Alternative technologies for the generation of adenovirus include utilization of the bacterial artificial chromosome (BAC) system, in vivo bacterial recombination in a recA bacterial strain utilizing two plasmids containing complementary, adenoviral sequences, and the yeast artificial chromosome (YAC) system.

II. Therapeutic Transgenes

A recombinant virus, e.g., a recombinant oncolytic adenovirus, produced using a method disclosed herein may comprise an exogenous nucleotide sequence that encodes for a therapeutic transgene. The term "transgene" refers to an exogenous gene or polynucleotide sequence. The term "therapeutic transgene" refers to a transgene, which when replicated and/or expressed in or by the virus imparts a therapeutic effect in a target cell, body fluid, tissue, organ, physiological system, or subject.

The therapeutic transgene may encode a therapeutic nucleic acid, e.g., an antisense RNA or ribozyme RNA. The therapeutic transgene may encode a therapeutic peptide or polypeptide, e.g., an apoptotic agent, antibody, CTL responsive peptide, cytokine, cytolytic agent, cytotoxic agent, enzyme, heterologous antigen expressed on the surface of a tumor cell to elicit an immune response, immunostimulatory or immunomodulatory agent, interferon, lytic peptide, oncoprotein, polypeptide which catalyzes processes leading to cell death, polypeptide which complements genetic defects in somatic cells, tumor suppressor protein, vaccine antigen, or any combination thereof.

In certain embodiments, the therapeutic transgene encodes a therapeutic polypeptide selected from CD80, CD137L, IL-23, IL-23A/p19, p40, IL-27, IL-27A/p28, IL-27B/EBI3, ICAM-1, a TGF-β trap, TGF-β, CD19, CD20, IL-1, IL-3, IL-4, IL-5, IL-6, IL-8, IL-9, CD154, CD86, BORIS/CTCFL, FGF, IL-24, MAGE, NY-ESO-1, acetylcholine, interferon-gamma, DKK1/Wnt, p53, thymidine kinase, an anti-PD-1 antibody heavy chain or light chain, and an anti-PD-L1 antibody heavy chain or light chain.

III. Pharmaceutical Compositions

For therapeutic use, a recombinant virus, e.g., a recombinant oncolytic adenovirus, produced using a method disclosed herein is preferably combined with a pharmaceutically acceptable carrier. As used herein, "pharmaceutically acceptable carrier" means buffers, carriers, and excipients suitable for use in contact with the tissues of human beings and animals without excessive toxicity, irritation, allergic response, or other problem or complication, commensurate with a reasonable benefit/risk ratio. The carrier(s) should be "acceptable" in the sense of being compatible with the other ingredients of the formulations and not deleterious to the recipient. Pharmaceutically acceptable carriers include buffers, solvents, dispersion media, coatings, isotonic and absorption delaying agents, and the like, that are compatible with pharmaceutical administration. The use of such media and agents for pharmaceutically active substances is known in the art.

Pharmaceutical compositions containing recombinant viruses can be presented in a dosage unit form and can be prepared by any suitable method. A pharmaceutical composition should be formulated to be compatible with its intended route of administration. Examples of routes of administration are intravenous (IV), intraarterial, intradermal, inhalation, transdermal, topical, transmucosal, and rectal administration. A preferred route of administration is IV infusion. Useful formulations can be prepared by methods known in the pharmaceutical art. For example, see *Remington's Pharmaceutical Sciences,* 18th ed. (Mack Publishing Company, 1990). Formulation components suitable for parenteral administration include a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as EDTA; buffers such as acetates, citrates or phosphates; and agents for the adjustment of tonicity such as sodium chloride or dextrose.

For intravenous administration, suitable carriers include physiological saline, bacteriostatic water, Cremophor ELTM (BASF, Parsippany, NJ) or phosphate buffered saline (PBS). The carrier should be stable under the conditions of manufacture and storage, and should be preserved against microorganisms. The carrier can be a solvent or dispersion medium containing, for example, water, ethanol, polyol (for example, glycerol, propylene glycol, and liquid polyethey-lene glycol), and suitable mixtures thereof.

Pharmaceutical formulations preferably are sterile. Sterilization can be accomplished by any suitable method, e.g., filtration through sterile filtration membranes. Where the composition is lyophilized, filter sterilization can be conducted prior to or following lyophilization and reconstitution.

The term "effective amount" as used herein refers to the amount of an active component (e.g., the amount of a recombinant virus) sufficient to effect beneficial or desired results. An effective amount can be administered in one or more administrations, applications or dosages and is not intended to be limited to a particular formulation or administration route.

In certain embodiments, a therapeutically effective amount of active component is in the range of 0.1 mg/kg to 100 mg/kg, e.g., 1 mg/kg to 100 mg/kg, 1 mg/kg to 10 mg/kg. In certain embodiments, a therapeutically effective amount of the recombinant virus is in the range of $10^2$ to $10^{15}$ plaque forming units (pfus), e.g., $10^2$ to $10^{10}$, $10^2$ to $10^5$, $10^5$ to $10^{15}$, $10^5$ to $10^{10}$, or $10^{10}$ to $10^{15}$ plaque forming units. The amount administered will depend on variables such as the type and extent of disease or indication to be treated, the overall health of the patient, the in vivo potency of the virus, the pharmaceutical formulation, and the route of administration. The initial dosage can be increased beyond the upper level in order to rapidly achieve the desired blood-level or tissue-level. Alternatively, the initial dosage can be smaller than the optimum, and the daily dosage may be progressively increased during the course of treatment. Human dosage can be optimized, e.g., in a conventional Phase I dose escalation study designed to run from 0.5 mg/kg to 20 mg/kg. Dosing frequency can vary, depending on factors such as route of administration, dosage amount, serum half-life of the virus, and the disease being treated. Exemplary dosing frequencies are once per day, once per week and once every two weeks. A preferred route of administration is parenteral, e.g., intravenous infusion.

IV. Therapeutic Uses

A recombinant virus, e.g., a recombinant oncolytic adenovirus produced using a method disclosed herein, can be used to treat various medical indications, for example, cancers. As used herein, "treat", "treating" and "treatment" mean the treatment of a disease in a subject, e.g., in a human. This includes: (a) inhibiting the disease, i.e., arresting its development; and (b) relieving the disease, i.e., causing regression of the disease state. As used herein, the terms "subject" and "patient" refer to an organism to be treated by the methods and compositions described herein. Such organisms preferably include, but are not limited to, mammals (e.g., murines, simians, equines, bovines, porcines, canines, felines, and the like), and more preferably includes humans.

Examples of cancers include solid tumors, soft tissue tumors, hematopoietic tumors and metastatic lesions. Examples of hematopoietic tumors include, leukemia, acute leukemia, acute lymphoblastic leukemia (ALL), B-cell, T-cell or FAB ALL, acute myeloid leukemia (AML), chronic myelocytic leukemia (CML), chronic lymphocytic leukemia (CLL), e.g., transformed CLL, diffuse large B-cell lymphomas (DLBCL), follicular lymphoma, hairy cell leukemia, myelodyplastic syndrome (MDS), a lymphoma, Hodgkin's disease, a malignant lymphoma, non-Hodgkin's lymphoma, Burkitt's lymphoma, multiple myeloma, or Richter's Syndrome (Richter's Transformation). Examples of solid tumors include malignancies, e.g., sarcomas, adenocarcinomas, and carcinomas, of the various organ systems, such as those affecting head and neck (including pharynx), thyroid, lung (small cell or non-small cell lung carcinoma (NSCLC)), breast, lymphoid, gastrointestinal (e.g., oral, esophageal, stomach, liver, pancreas, small intestine, colon and rectum, anal canal), genitals and genitourinary tract (e.g., renal, urothelial, bladder, ovarian, uterine, cervical, endometrial, prostate, testicular), CNS (e.g., neural or glial cells, e.g., neuroblastoma or glioma), or skin (e.g., melanoma).

In certain embodiments, the cancer is selected from melanoma, squamous cell carcinoma of the skin, basal cell carcinoma, head and neck cancer, breast cancer, anal cancer, cervical cancer, non-small cell lung cancer, mesothelioma, small cell lung cancer, renal cell carcinoma, prostate cancer, gastroesophageal cancer, colorectal cancer, testicular cancer, bladder cancer, ovarian cancer, hepatocellular carcinoma, cholangiocarcinoma, brain cancer, endometrial cancer, neuroendocrine cancer, and pancreatic cancer.

In certain embodiments, the cancer is selected from nasopharyngeal cancer, basal cell carcinoma, synovial cancer, hepatocellular cancer, renal cancer, cancer of connective tissues, melanoma, lung cancer, bowel cancer, colon cancer, rectal cancer, colorectal cancer, brain cancer, throat cancer, oral cancer, liver cancer, bone cancer, pancreatic cancer, choriocarcinoma, gastrinoma, neuroendocrine, pheochromocytoma, prolactinoma, T-cell leukemia/lymphoma, neuroma, von Hippel-Lindau disease, Zollinger-Ellison syndrome, adrenal cancer, anal cancer, bile duct cancer, bladder cancer, ureter cancer, brain cancer, oligodendroglioma, neuroblastoma, meningioma, spinal cord tumor, bone cancer, osteochondroma, chondrosarcoma, Ewing's sarcoma, cancer of unknown primary site, carcinoid, carcinoid of gastrointestinal tract, fibrosarcoma, breast cancer, Paget's disease, cervical cancer, colorectal cancer, rectal cancer, esophagus cancer, gall bladder cancer, head cancer, eye cancer, neck cancer, kidney cancer, Wilms' tumor, liver cancer, Kaposi's sarcoma, prostate cancer, lung cancer, testicular cancer, Hodgkin's disease, non-Hodgkin's lymphoma, oral cancer, skin cancer, mesothelioma, multiple myeloma, ovarian cancer, endocrine pancreatic cancer, glucagonoma, pancreatic cancer, parathyroid cancer, penis cancer, pituitary cancer, soft tissue sarcoma, retinoblastoma, small intestine cancer, stomach cancer, thymus cancer, thyroid cancer, trophoblastic cancer, hydatidiform mole, uterine cancer, endometrial cancer, vagina cancer, vulva cancer, acoustic neuroma, mycosis fungoides, insulinoma, carcinoid syndrome, somatostatinoma, gum cancer, heart cancer, lip cancer, meninges cancer, mouth cancer, nerve cancer, palate cancer, parotid gland cancer, peritoneum cancer, pharynx cancer, pleural cancer, salivary gland cancer, tongue cancer and tonsil cancer.

In certain embodiments, a recombinant virus, e.g., a recombinant oncolytic adenovirus, is administered to the subject in combination with one or more therapies, e.g., surgery, radiation, chemotherapy, immunotherapy, hormone therapy, or virotherapy. In certain embodiments, a recombinant virus is administered in combination with a tyrosine kinase inhibitor, e.g., erlotinib. In certain embodiments, a recombinant virus of the invention is administered in combination with a checkpoint inhibitor, e.g., an anti-CTLA-4 antibody, an anti-PD-1 antibody, or an anti-PD-L1 antibody. Exemplary anti-PD-1 antibodies include, for example, nivolumab (Opdivo®, Bristol-Myers Squibb Co.), pembrolizumab (Keytruda®, Merck Sharp & Dohme Corp.), PDR001 (Novartis Pharmaceuticals), and pidilizumab (CT-011, Cure Tech). Exemplary anti-PD-L1 antibodies include, for example, atezolizumab (Tecentriq®, Genentech), duvalumab (AstraZeneca), MEDI4736, avelumab, and BMS 936559 (Bristol Myers Squibb Co.).

The term administered "in combination," as used herein, is understood to mean that two (or more) different treatments are delivered to the subject during the course of the subject's affliction with the disorder, such that the effects of the treatments on the patient overlap at a point in time. In certain embodiments, the delivery of one treatment is still occurring when the delivery of the second begins, so that there is overlap in terms of administration. This is sometimes referred to herein as "simultaneous" or "concurrent delivery." In other embodiments, the delivery of one treatment ends before the delivery of the other treatment begins. In some embodiments of either case, the treatment is more effective because of combined administration. For example, the second treatment is more effective, e.g., an equivalent effect is seen with less of the second treatment, or the second treatment reduces symptoms to a greater extent, than would be seen if the second treatment were administered in the absence of the first treatment, or the analogous situation is seen with the first treatment. In certain embodiments, delivery is such that the reduction in a symptom, or other parameter related to the disorder is greater than what would be observed with one treatment delivered in the absence of the other. The effect of the two treatments can be partially additive, wholly additive, or greater than additive. The delivery can be such that an effect of the first treatment delivered is still detectable when the second is delivered.

Throughout the description, where viruses, compositions and systems are described as having, including, or comprising specific components, or where processes and methods are described as having, including, or comprising specific steps, it is contemplated that, additionally, there are compositions, devices, and systems of the present invention that consist essentially of, or consist of, the recited components, and that there are processes and methods according to the present invention that consist essentially of, or consist of, the recited processing steps.

In the application, where an element or component is said to be included in and/or selected from a list of recited elements or components, it should be understood that the element or component can be any one of the recited elements or components, or the element or component can be selected from a group consisting of two or more of the recited elements or components.

Further, it should be understood that elements and/or features of a virus, a composition, a system, a method, or a process described herein can be combined in a variety of ways without departing from the spirit and scope of the present invention, whether explicit or implicit herein. For example, where reference is made to a particular virus, that virus can be used in various embodiments of compositions of the present invention and/or in methods of the present invention, unless otherwise understood from the context. In other words, within this application, embodiments have been described and depicted in a way that enables a clear and concise application to be written and drawn, but it is intended and will be appreciated that embodiments may be variously combined or separated without parting from the present teachings and invention(s). For example, it will be appreciated that all features described and depicted herein can be applicable to all aspects of the invention(s) described and depicted herein.

It should be understood that the expression "at least one of" includes individually each of the recited objects after the expression and the various combinations of two or more of the recited objects unless otherwise understood from the context and use. The expression "and/or" in connection with three or more recited objects should be understood to have the same meaning unless otherwise understood from the context.

The use of the term "include," "includes," "including," "have," "has," "having," "contain," "contains," or "containing," including grammatical equivalents thereof, should be understood generally as open-ended and non-limiting, for example, not excluding additional unrecited elements or steps, unless otherwise specifically stated or understood from the context.

At various places in the present specification, viruses, compositions, systems, processes and methods, or features thereof, are disclosed in groups or in ranges. It is specifically intended that the description include each and every individual subcombination of the members of such groups and ranges. By way of other examples, an integer in the range of 1 to 20 is specifically intended to individually disclose 1, 2, 3, 4, 5, 6, 7, 8, 9, 10, 11, 12, 13, 14, 15, 16, 17, 18, 19, and 20.

Where the use of the term "about" is before a quantitative value, the present invention also includes the specific quantitative value itself, unless specifically stated otherwise. As used herein, the term "about" refers to a ±10% variation from the nominal value unless otherwise indicated or inferred.

It should be understood that the order of steps or order for performing certain actions is immaterial so long as the present invention remain operable. Moreover, two or more steps or actions may be conducted simultaneously.

The use of any and all examples, or exemplary language herein, for example, "such as" or "including," is intended merely to illustrate better the present invention and does not pose a limitation on the scope of the invention unless claimed. No language in the specification should be construed as indicating any non-claimed element as essential to the practice of the present invention.

EXAMPLES

The following Examples are merely illustrative and are not intended to limit the scope or content of the invention in any way.

Example 1: Production of an Oncolytic Adenovirus

This Example describes the production of a recombinant oncolytic adenovirus in A549 cells.

An adenovirus type 5 virus was constructed that carries the deletion of a nucleotide region located from −304 to −255 upstream of the E1a initiation site, which renders E1a expression cancer-selective (as previously described in U.S. Pat. No. 9,073,980). The resulting virus is hereafter referred to as TAV.

TAV was further modified to carry an approximately 200 base pair deletion in the E1b-19k region. The resulting virus is hereafter referred to as TAV-Δ19k. The nucleotide sequence of the modified E1b-19k region is as follows, with residual bases from fused SalI and XhoI sites underlined:

(SEQ ID NO: 6)
ATCTTGGTTACATCTGACCTC<u>GTCGAG</u>TCACCAGGCGCTTTTCCAA

TAV-Δ19k was modified to include a nucleotide sequence encoding a mouse TGF-β trap (a fusion protein of the mouse TGFβ type II receptor and mouse IgG1) in the modified E1b-19k region. The resulting virus is hereafter referred to as TAV-mTGFβ-Trap. The nucleotide sequence encoding the TGF-β trap is as follows:

(SEQ ID NO: 7)
ATGGGTCGGGGGCTGCTCCGGGGCCTGTGGCCGCTGCATATCGTCCTGTG

GACGCGCATCGCCAGCACGATCCCGCCGCACGTTCCCAAGTCGGTTAACA

GTGATGTCATGGCCAGCGACAATGGCGGTGCGGTCAAGCTTCCACAGCTG

TGCAAGTTTTGCGATGTGAGACTGTCCACTTGCGACAACCAGAAGTCCTG

CATGAGCAACTGCAGCATCACGGCCATCTGTGAGAAGCCGCATGAAGTCT

GCGTGGCCGTGTGGAGGAAGAACGACAAGAACATTACTCTGGAGACGGTT

TGCCACGACCCCAAGCTCACCTACCACGGCTTCACTCTGGAAGATGCCGC

TTCTCCCAAGTGTGTCATGAAGGAAAAGAAAAGGGCGGGCGAGACTTTCT

TCATGTGTGCCTGTAACATGGAAGAGTGCAACGATTACATCATCTTTTCG

GAAGAATACACCACCAGCAGTCCCGACAGCACCAAGGTGGACAAGAAAAT

TGTGCCCAGGGATTGTGGTTGTAAGCCTTGCATATGTACAGTCCCAGAAG

TATCATCTGTCTTCATCTTCCCCCCAAAGCCCAAGGATGTGCTCACCATT

ACTCTGACTCCTAAGGTCACGTGTGTTGTGGTAGACATCAGCAAGGATGA

TCCCGAGGTCCAGTTCAGCTGGTTTGTAGATGATGTGGAGGTGCACACAG

CTCAGACGCAACCCCGGGAGGAGCAGTTCAACAGCACTTTCCGCTCAGTC

AGTGAACTTCCCATCATGCACCAGGACTGGCTCAATGGCAAGGAGTTCAA

ATGCAGGGTCAACAGTGCAGCTTTCCCTGCCCCCATCGAGAAAACCATCT

CCAAAACCAAAGGCAGACCGAAGGCTCCGCAGGTGTACACCATTCCACCT

CCCAAGGAGCAGATGGCCAAGGATAAAGTCAGTCTGACCTGCATGATAAC

AGACTTCTTCCCTGAAGACATTACTGTGGAGTGGCAGTGGAATGGGCAGC

CAGCGGAGAACTACAAGAACACTCAGCCCATCATGGACACAGATGGCTCT

TACTTCGTCTACAGCAAGCTCAATGTGCAGAAGAGCAACTGGGAGGCAGG

AAATACTTTCACCTGCTCTGTGTTACATGAGGGCCTGCACAACCACCATA

CTGAGAAGAGCCTCTCCCACTCTCCTGGTAAATGA

SF-BMAdR 281 A549 cells (purchased from National Research Council of Canada) were cultured in serum-free media (Hyclone SFM4Transfx-293) in suspension culture in shake flasks. After growth to a density of $2 \times 10^6$ cells/mL in a total volume of 100 mL, the cells were centrifuged and resuspended in 100 mL of fresh SFM4Transfx-293 media. 50 mL of the resuspended culture was infected with the TAV-Δ19k adenovirus, and 50 mL of the resuspended culture was infected with the TAV-mTGFβ-Trap adenovirus. The cells were maintained in suspension culture in shake flasks for three days to allow for viral replication, and the cultures were then lysed with freeze-thaw cycles to produce cell lysate.

The viruses were then purified from the cell lysate by centrifugation, nuclease treatment, anion exchange chromatography, and dialysis into a buffer appropriate for in vivo administration (10 mM Tris, 1 mM $MgCl_2$, 3% sucrose, pH 8).

Figure 2:
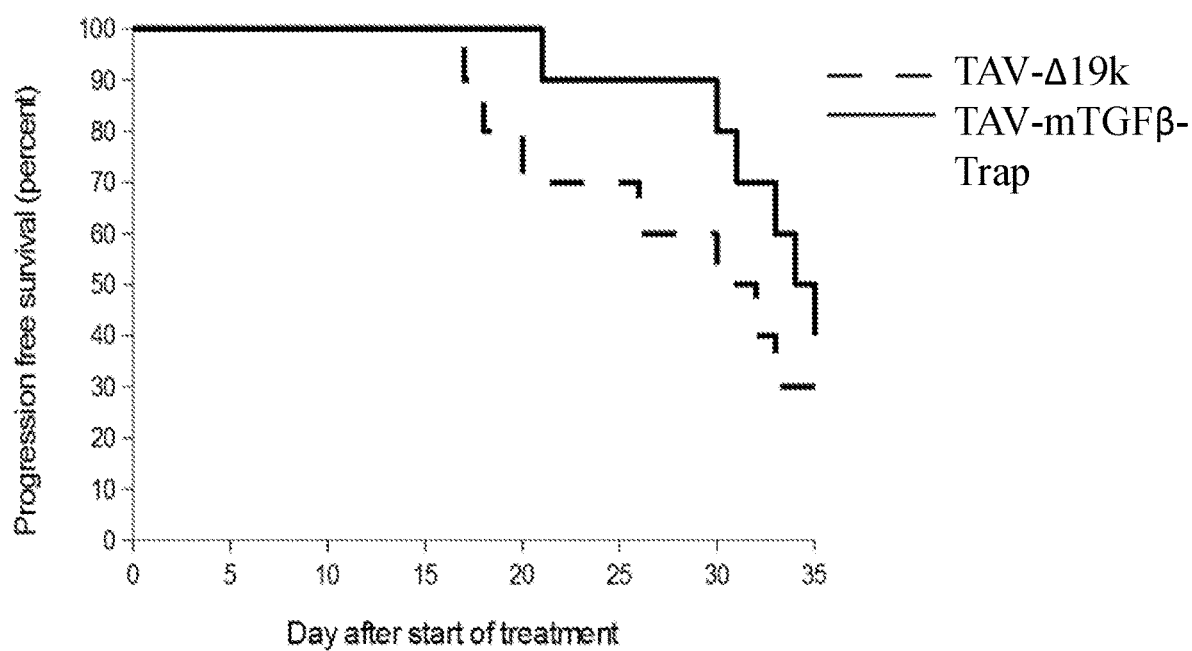
FIG. 2 is a line graph depicting progression free survival of mice treated with the indicated virus. Progression is defined as tumor volume exceeding 200 mm$^3$.

The viruses were then tested for efficacy in vivo. Adult 129S4 mice were injected subcutaneously with $1 \times 10^6$ ADS-12 cells, a pulmonary cancer cell line, and allowed to form subcutaneous tumors. After the tumors grew large enough to treat, 10 mice each were treated with intratumoral injections of either the TAV-Δ19k adenovirus or the TAV-mTGFβ-Trap adenovirus. Three doses of $1 \times 10^9$ IU of each virus were administered every four days. Mean tumor volume in mice treated with each virus is depicted in FIG. 1, and progression free survival of mice treated with each virus is depicted in FIG. 2.

Example 2: Production of an Oncolytic Adenovirus

This Example describes the production of a recombinant oncolytic adenovirus in A549 derived cells relative to HEK-293 derived cells.

An adenovirus type 5 virus was constructed that carries the deletion of a nucleotide region located from −304 to −255 upstream of the E1a initiation site, which renders E1a expression cancer-selective (as previously described in U.S. Pat. No. 9,073,980). The resulting virus is hereafter referred to as TAV.

TAV was further modified to carry an approximately 200 base pair deletion in the E1b-19k region. The resulting virus is hereafter referred to as TAV-Δ19k. The nucleotide sequence of the modified E1b-19k region is as follows, with residual bases from fused SalI and XhoI sites underlined:

(SEQ ID NO: 6)
ATCTTGGTTACATCTGACCTCGTCGAGTCACCAGGCGCTTTTCCAA

TAV-Δ19k was modified to include a nucleotide sequence encoding a human TGF-β trap (a fusion protein of the human TGFβ type II receptor and human IgG1) in the modified E1b-19k region. The resulting virus is hereafter referred to as TAV-hTGFβ-Trap.

Figure 3:
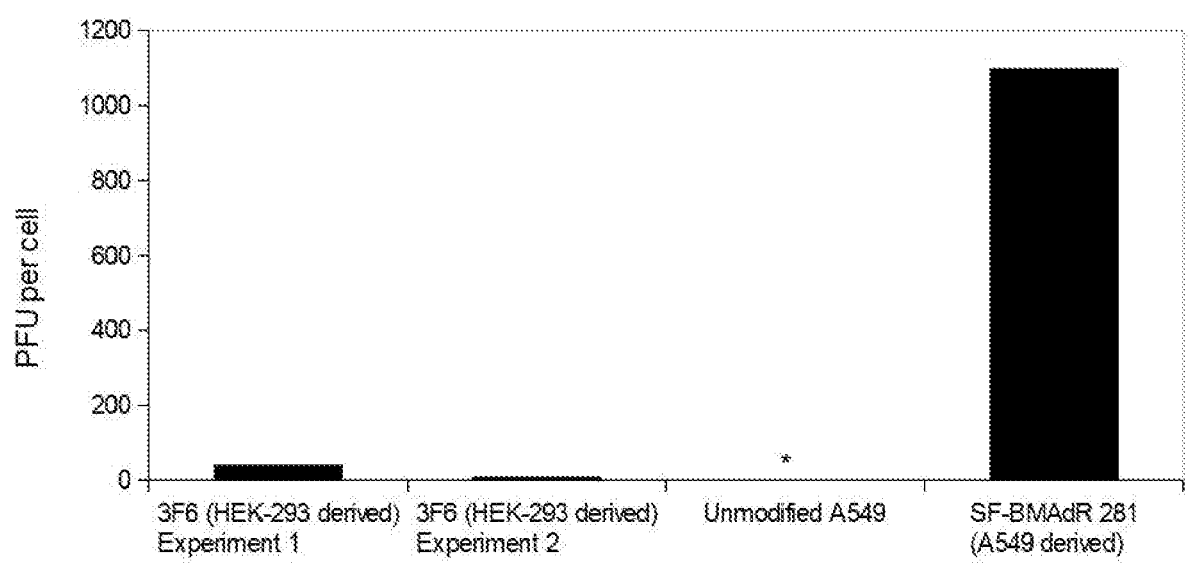
FIG. 3 depicts viral production from a HEK-293 derived cell line and the SF-BMAdR 281 (A549 derived) cell line. No results were available for unmodified A549 cells because they could not be adapted to serum-free suspension culture.

TAV-hTGFβ-Trap adenovirus was produced in both HEK-293 cells (293-3F6) and A549 cells (SF-BMAdR). HEK-293 cells cultured in serum-free medium (SFM4Transfx-293) at $5 \times 10^5$ cells/mL were infected with TAV-hTGFβ-Trap at a multiplicity of infection (MOI) of 3. At 4 days post-infection the yield was 42 PFU/cell. In a separate experiment, HEK-293 cells cultured in serum-free medium (SFM4Transfx-293) at $1 \times 10^6$ cells/mL were infected with TAV-hTGFβ-Trap at an MOI of 3. At 4 days post-infection the yield was less than 10 PFU/cell. A549 cells cultured in serum-free medium (SFM4Transfx-293) at $1 \times 10^6$ cells/mL were infected with TAV-hTGFβ-Trap at an MOI of 3. At 4 days post-infection the yield was 1100 PFU/cell. Unmodified A549 cells could not be adapted to grow in the same serum-free medium (SFM4Transfx-293) in suspension culture. Viral production from these cell lines is depicted in FIG. 3.

Together, these results show that A549 derived host cells, e.g., SF-BMAdR A549 host cells, produce greater yields of certain oncolytic viruses, e.g., the TAV-hTGFβ-Trap adenovirus.

INCORPORATION BY REFERENCE

The entire disclosure of each of the patent documents and scientific articles referred to herein is incorporated by reference for all purposes.

EQUIVALENTS

The invention may be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes that come within the meaning and the range of equivalency of the claims are intended to be embraced therein.

What is claimed is:

1. A method for producing a recombinant oncolytic adenovirus comprising:
   (a) infecting an A549 host cell with the recombinant oncolytic adenovirus to produce an infected A549 host cell or introducing a nucleic acid comprising a nucleotide sequence encoding the recombinant oncolytic adenovirus into an A549 host cell; and
   (b) suspension culturing the A549 host cell in a serum-free medium, under conditions to permit production of the recombinant oncolytic adenovirus,
   wherein the recombinant oncolytic adenovirus comprises an E1a gene comprising an E1a protein coding region operably linked to a modified regulatory sequence comprising (i) deletion of a functional Pea3 binding site, (ii) deletion of a functional E2F binding site, (iii) deletion of a functional TATA box, (iv) deletion of a functional CAAT box, (v) deletion of the nucleotides corresponding to the nucleotides from 195-244 of the Ad5 genome (SEQ ID NO: 1), or (vi) has two, three, or four of (i), (ii), (iii), and (iv).

2. The method of claim 1, wherein the A549 host cell is a SF-BMAdR 281 A549 cell.

3. The method of claim 1, wherein the A549 host cell is cultured for at least 3 days.

4. The method of claim 1, further comprising, after step (b), the step of purifying the recombinant oncolytic adenovirus.

5. The method of claim 4, wherein the step of purifying the recombinant oncolytic adenovirus comprises lysing the A549 host cell.

6. The method of claim 4, wherein the step of purifying the recombinant oncolytic adenovirus comprises nuclease treatment.

7. The method of claim 4, wherein the step of purifying the recombinant oncolytic adenovirus comprises ion exchange chromatography.

8. The method of claim 7, wherein the step of purifying the recombinant oncolytic adenovirus comprises: (i) lysing the infected A549 host cell to produce a cell lysate; (ii) treating the cell lysate with nuclease to produce a treated cell lysate; and (iii) purifying the recombinant virus from the treated cell lysate by ion exchange chromatography.

9. The method of claim 1, wherein the method results in at least 10× more recombinant oncolytic adenovirus compared to a similar method that comprises, in step (a), introducing a nucleic acid comprising a nucleotide sequence encoding a recombinant oncolytic virus into a HEK293 host, and, in step (b), suspension culturing the HEK293 host cell in a serum-free medium, under conditions to permit production of the recombinant oncolytic adenovirus.

10. The method of claim 1, wherein the method results in at least 10× more recombinant oncolytic adenovirus compared to a similar method that comprises, in step (b), adherent culturing the A549 host cell in a serum-free medium, under conditions to permit replication of the recombinant oncolytic adenovirus.

11. The method of claim 1, wherein the method results in at least 10× more recombinant oncolytic adenovirus compared to a similar method that comprises, in step (b), suspension culturing the A549 host cell in a serum-containing medium, under conditions to permit replication of the recombinant oncolytic adenovirus.

12. The method of claim 1, wherein the E1a promoter has the deletion of a functional Pea3 binding site.

13. The method of claim 1, wherein the E1a promoter has the deletion of a functional TATA box.

14. The method of claim 1, wherein the recombinant oncolytic adenovirus comprises a polynucleotide deletion that results in a virus sequence comprising the junction sequence corresponding to CTAGGACTG (SEQ ID NO: 3), AGTGCCCG (SEQ ID NO: 8) and/or TATTCCCG (SEQ ID NO: 9) of the Ad5 genome (SEQ ID NO: 1).

15. The method of claim 1, wherein the E1a promoter has the deletion of a functional CAAT box.

16. The method of claim 1, wherein the recombinant oncolytic adenovirus comprises a nucleotide sequence encoding a transgene.

17. The method of claim 16, wherein the nucleotide sequence is inserted into an E1b-19K insertion site, and wherein the E1b-19K insertion site is located between the start site of E1b-19K and the stop site of E1b-19K.

18. The method of claim 16, wherein the transgene is not operably linked to an exogenous promoter sequence and/or the recombinant virus selectively expresses the transgene in a hyperproliferative cell.

19. The method of claim 16, wherein the transgene encodes a polypeptide selected from CD80, CD137L, IL-23, IL-23A/p19, p40, IL-27, IL-27A/p28, IL-27B/EBI3, ICAM-1, a TGF-β Trap, TGF-β, CD19, CD20, IL-1, IL-3, IL-4, IL-5, IL-6, IL-8, IL-9, CD154, CD86, BORIS/CTCFL, FGF, IL-24, MAGE, NY-ESO-1, acetylcholine, interferon-gamma, DKK1/Wnt, p53, thymidine kinase, an anti-PD-1 antibody heavy chain or light chain, and an anti-PD-L1 antibody heavy chain or light chain.

20. The method of claim 1, wherein the recombinant virus selectively replicates in a hyperproliferative cell.

21. The method of claim 1, wherein the Pea3 binding site is selected from Pea3 I, Pea3 II, Pea3 III, Pea3 IV, and Pea3 V.

22. The method of claim 1, wherein the E2F binding site is selected from E2F I and E2F II.

23. The method of claim 1, wherein the recombinant oncolytic adenovirus is a type 5 adenovirus (Ad5).

\* \* \* \* \*